(12) United States Patent
Brown

(10) Patent No.: US 11,324,903 B2
(45) Date of Patent: May 10, 2022

(54) TO THE MANUFACTURE AND REMANUFACTURE OF VOLATILE ANAESTHETIC AGENTS USING SUPERCRITICAL FLUIDS

(71) Applicant: SAGETECH MEDICAL EQUIPMENT LIMITED, West Byfleet (GB)

(72) Inventor: Sebastian Brown, Totnes (GB)

(73) Assignee: SAGETECH MEDICAL EQUIPMENT LIMITED, West Byfleet (GB)

( * ) Notice: Subject to any disclaimer, the term of this patent is extended or adjusted under 35 U.S.C. 154(b) by 279 days.

(21) Appl. No.: 16/077,814

(22) PCT Filed: Feb. 22, 2017

(86) PCT No.: PCT/GB2017/050460
§ 371 (c)(1),
(2) Date: Aug. 14, 2018

(87) PCT Pub. No.: WO2017/144879
PCT Pub. Date: Aug. 31, 2017

(65) Prior Publication Data
US 2019/0275275 A1   Sep. 12, 2019

(30) Foreign Application Priority Data

Feb. 23, 2016   (GB) .................................... 1603050

(51) Int. Cl.
| | | |
|---|---|---|
| A61M 16/00 | (2006.01) | |
| A61M 16/18 | (2006.01) | |
| B01D 53/04 | (2006.01) | |
| B01D 53/047 | (2006.01) | |
| B01J 20/10 | (2006.01) | |
| B01J 20/20 | (2006.01) | |
| B01J 20/28 | (2006.01) | |
| B01J 20/18 | (2006.01) | |
| A61M 16/01 | (2006.01) | |

(52) U.S. Cl.
CPC ........ *A61M 16/0093* (2014.02); *A61M 16/01* (2013.01); *A61M 16/18* (2013.01);
(Continued)

(58) Field of Classification Search
CPC ........ B01D 2259/4533; B01D 53/0415; B01D 53/0446; B01D 53/047; B01D 2253/102;
(Continued)

(56) References Cited

U.S. PATENT DOCUMENTS 3,830,632 A * 8/1974 Guzay .................... B01D 53/62
422/120
3,867,936 A * 2/1975 Kelley ................ A61M 16/009
128/205.12
(Continued)

FOREIGN PATENT DOCUMENTS

CN   105884587   8/2016
DE   102006008320   8/2007
(Continued)

OTHER PUBLICATIONS

Search Report, dated Dec. 7, 2016, in GB1603094.2.
(Continued)

*Primary Examiner* — Timothy A Stanis
*Assistant Examiner* — Benjamin M. Kusiak
(74) *Attorney, Agent, or Firm* — Thomas | Horstemeyer, LLP

(57) ABSTRACT

An anaesthetic halocarbon capture system is provided. The system includes a pressure-intolerant sleeve containing filter material for capturing one or more types of anaesthetic halocarbon prior to supercritical fluid extraction, and a pressure-tolerant housing into which the sleeve can be inserted so as to permit exposure of the sleeve contents to pressures required for supercritical fluid extraction.

13 Claims, 15 Drawing Sheets

(52) U.S. Cl.
CPC ....... *B01D 53/047* (2013.01); *B01D 53/0415* (2013.01); *B01D 53/0446* (2013.01); *B01J 20/103* (2013.01); *B01J 20/18* (2013.01); *B01J 20/20* (2013.01); *B01J 20/28004* (2013.01); *B01J 20/28047* (2013.01); *B01D 2253/102* (2013.01); *B01D 2253/106* (2013.01); *B01D 2253/108* (2013.01); *B01D 2253/25* (2013.01); *B01D 2257/206* (2013.01); *B01D 2257/504* (2013.01); *B01D 2258/06* (2013.01); *B01D 2259/40084* (2013.01); *B01D 2259/40086* (2013.01); *B01D 2259/4508* (2013.01); *B01D 2259/4533* (2013.01); *Y02C 20/40* (2020.08)

(58) Field of Classification Search
CPC ............ B01D 2253/25; B01D 2258/06; B01D 2253/108; B01D 2259/40084; B01D 2259/4508; B01D 2253/106; B01D 2257/206; B01D 2257/504; B01D 2259/40086; B01D 53/1418; B01D 53/1487; B01D 53/68–685; B01D 2201/202; B01D 2201/291–298; B01D 2201/301–306; B01D 2259/40013–40018; B01D 53/04; B01D 53/0423; B01D 54/0415; A61P 23/00; A61M 16/0093; A61M 16/01; A61M 16/18; B01J 20/18; B01J 20/103; B01J 20/20; B01J 20/28004; B01J 20/28047; Y02C 10/08
USPC ................. 55/359, 367, 369–371, 374–377; 95/82–89, 43–56, 141–147, 273–287, 95/131; 96/4–14, 101–107, 108–154
See application file for complete search history.

(56) References Cited

U.S. PATENT DOCUMENTS

| | | | |
|---|---|---|---|
| 3,941,573 A | 3/1976 | Chapel | |
| 4,874,901 A | 10/1989 | Halpern | |
| 4,905,685 A * | 3/1990 | Olsson | A61M 16/009 128/203.12 |
| 5,039,500 A * | 8/1991 | Shino | F25J 3/04757 423/262 |
| 5,231,980 A * | 8/1993 | Filipovic | A61M 16/0087 128/205.12 |
| 6,235,192 B1 * | 5/2001 | Melfi | B01D 35/15 137/856 |
| 7,644,594 B2 * | 1/2010 | Berry | A61M 16/009 62/617 |
| 8,242,317 B2 * | 8/2012 | Stach | A61M 16/0093 570/262 |
| 9,861,927 B2 * | 1/2018 | Neto | B01D 53/0407 |
| 2009/0101010 A1 | 4/2009 | Fuesting | |
| 2009/0250054 A1 * | 10/2009 | Loncar | A61M 16/0093 128/203.14 |
| 2010/0263529 A1 * | 10/2010 | Alban | B01D 53/002 95/41 |
| 2011/0081379 A1 * | 4/2011 | Kurosawa | C12N 7/00 424/218.1 |
| 2011/0192192 A1 * | 8/2011 | Andrian | F25J 3/0635 62/620 |
| 2012/0000549 A1 * | 1/2012 | Thorne | B01D 53/266 137/455 |
| 2012/0024152 A1 * | 2/2012 | Yamawaki | B01D 53/0438 95/96 |
| 2012/0222556 A1 * | 9/2012 | Filipovic | C07C 41/34 95/142 |
| 2015/0283490 A1 * | 10/2015 | Cordova | B01D 46/0023 96/136 |
| 2015/0336042 A1 | 11/2015 | Welke | |
| 2017/0173231 A1 * | 6/2017 | Kiriyama | A61M 1/38 |
| 2017/0252682 A1 * | 9/2017 | Gustafson | B01D 35/005 |

FOREIGN PATENT DOCUMENTS

| | | |
|---|---|---|
| DE | 102006027127 | 12/2007 |
| EP | 0682980 | 11/1995 |
| WO | 2016027097 | 2/2016 |

OTHER PUBLICATIONS

Search Report, dated Jul. 27, 2016, in GB 1603053.8.
Search Report, dated Jul. 19, 2016, in GB 1603050.4.
International Search Report & Written Opinion. PCT/GB2017/050460, dated August 3, 2017.

* cited by examiner

TOP VIEW OF INLET

SIDE VIEW CUTOUT

TO THE MANUFACTURE AND REMANUFACTURE OF VOLATILE ANAESTHETIC AGENTS USING SUPERCRITICAL FLUIDS

RELATED APPLICATIONS

This application is the 35 U.S.C. § 371 national stage of PCT application having serial number PCT/GB2017/050460, filed on Feb. 22, 2017. This application also claims priority to GB application serial number 1603050.4 filed on Feb. 23, 2016; GB application serial number 1603053.8 filed on Feb. 23, 2016; GB application serial number 1603094.2 filed on Feb. 23, 2016; GB application serial number 1615173.0 filed on Sep. 7, 2016; GB application serial number 1617194.4 filed on Oct. 10, 2016; and GB application serial number 1618554.8 filed on Nov. 3, 2016, each of which are entirely incorporated herein by reference.

TECHNICAL FIELD

The present invention relates to methods and improvements in the capture of halocarbon volatile anaesthetic agents and their separation and purification for the purposes of re-supply to the consumer. This 'remanufacture' process is intended to provide financial and environmental cost savings. The present invention also relates to methods and improvements in the synthesis of valuable anaesthetic agents.

BACKGROUND

A halocarbon is an organic chemical molecule composed of at least one carbon atom bound covalently with one or more halogen elements. Halocarbons have many uses and are used in several industries as solvents, pesticides, refrigerants, fire-resistant oils, ingredients of elastomers, adhesives and sealants, electrically insulating coatings, plastics and anaesthetics. An alternative term for halocarbons is "halogenated fluorocarbons" when halogen elements other than fluorine are included in the molecule.

Volatile anaesthetic agents are typically halogenated fluorocarbons, examples of which include desflurane, isoflurane, sevoflurane and halothane. Volatile anaesthetic agents are liquid at room temperature but evaporate easily to produce a vapour for inhalation by a patient to induce anaesthesia. Anaesthetic agents are used extensively in modern healthcare and represent a significant cost. They are also potent greenhouse gases due to their ability to absorb infrared light and their upper atmospheric persistence. Isoflurane and Halothane also contain Chlorine and Bromine groups that contribute to ozone depletion.

Examples of halocarbons which are used as anaesthetic agents typically include desflurane, isoflurane, sevoflurane, halothane and enflurane. These anaesthetics may be referred to as volatile anaesthetic agents because they are liquid at room temperature but evaporate easily to produce a vapour for inhalation by a patient to induce anaesthesia. These agents are administered to patients using the breathing circuit of ananaesthetic machine, also known as a Boyle's machine. A schematic diagram of part of an anaesthetic machine including its breathing circuit 2 is described below with reference to FIG. 1. The primary function of the anaesthetic machine is to mix oxygen with volatile anaesthetic agent, at a clinician-specified concentration, for delivery to the patient via the breathing circuit 2.

The anaesthetic machine and breathing circuit 2 comprises a network of piped gas for inhalation by a patient (not shown). Air, oxygen ($O_2$) and nitrous oxide ($N_2O$) are supplied respectively to the back bar 15 from an air pipe 3 or an air cylinder pipe 5, an oxygen pipe 7 or an oxygen cylinder pipe 9 and a nitrous oxide pipe 11 or a nitrous oxide cylinder pipe 13. Each gas pipe 3, 7, 11 supplies gas at 4 bar. Air and oxygen are supplied by cylinderC pipes 5, 9, at 137 bar. Nitrous oxide is supplied by cylinder pipe 13 at 44 bar. To reduce the pressure of the gases supplied by the cylinder pipes 5, 9, 13 to match the pressure of the gases supplied by the gas pipe 3, 7, II each cylinder pipe 5, 9, 13 comprises a pressure reducing valve (PRV) 17 which reduces the pressure of gases supplied by the cylinder pipes 5, 9, 13 to 4 bar.

Each of the air, oxygen and nitrous oxide is delivered separately to a respective variable flow valve 19, which allows an anaesthetist to mix the air, oxygen and nitrous oxide as required. Each variable flow valve 19 further reduces the pressure of the gases to just over 1 bar. FIG. 1 shows the gases are delivered to the back bar 15, from left to right, via an air back bar pipe 18, an oxygen back bar pipe 20 and a nitrous oxide back bar pipe 22. It will be immediately apparent to the skilled person that the back bar pipes 18, 20, 22 may be arranged differently. For example, the back bar pipes 18, 20, 22 may be arranged from left to right, in FIG. 1 in the following order: the nitrous oxide back bar pipe 22; the oxygen back bar pipe 20; and the air back bar pipe 18. The back bar 15 comprises a vaporiser 10 and a pressure relief valve 16. The vaporizer 10 contains a vaporisation chamber 21 in which the agent 12 is housed. The vaporization chamber 21 is arranged so that the agent 12 evaporates to form vapour 14 at the saturated vapour pressure of the agent 12. For example, if the saturated vapour pressure is at too high a concentration to deliver agent 12 to the patient, a variable bypass valve 23 allows the anaesthetist to control the fraction of gases supplied from the back bar 15 that pass through the vaporiser 10. Accordingly, the output concentration of volatile agent 12 within the gas flow leaving the back bar 15 is controlled.

The patient inhales gases via a face mask 4 which fits over and forms a seal around the patient's nose and mouth. The face mask 4 is connected to an inspiratory tube 6 which supplies gases containing an anaesthetic agent 12, and an expiratory tube 8 through which exhaled and unused gases and agent 12 are transported away from the patient.

The inspiratory tube 6 and expiratory tube 8 are typically corrugated hoses.

The inspiratory tube 6 comprises a unidirectional inspiratory valve 25 which opens upon inhalation by the patient. When the unidirectional inspiratory valve 25 is in an open state, gas flows through the back bar 15, through the vaporisation chamber 10 where it mixes with vapour 14 from the agent 12. The gas mixed with agent vapour 14 is inhaled by the patient. In use, the breathing circuit 2 dispenses an accurate and continuous supply of anaesthetic agent mixed with oxygen/air/nitrous oxide ($N_2O$) at a specific concentration to the patient at a safe pressure and flow rate.

The expiratory tube 8 is connected to an expiratory pipe 24 to which is connected a unidirectional expiratory valve 26 through which exhaled and unused gases pass when the unidirectional expiratory valve 26 is open. Gas that passes through the unidirectional expiratory valve 26 flows into a breathing bag 28. An exhaust pipe 30 leads from the breathing bag 28 to a variable pressure-relief valve 32.

A carbon dioxide ($CO_2$) absorber canister 34 is connected to the expiratory pipe 24 and the inspiratory pipe 15 and arranged to allow gases to flow through the absorber canister 34 from the expiratory pipe 24 to the inspiratory pipe 6. The absorber canister 34 contains soda lime 36 which absorbs carbon dioxide from the gas that flows through the canister 34.

The configuration of the breathing circuit 2 illustrated in FIG. 1 is shown during inhalation of the gas/agent mixture by the patient. The movement of inhaled gases 15 is shown by the solid arrows and the movement of exhaled gases is shown using dashed arrows.

Inhalation by the patient causes the expiratory valve 26 to close and the inspiratory valve 25 to open. This allows recirculated gas to flow from the breathing bag 28, through the 20 absorption canister 34 which absorbs $CO_2$ in the gas, and into the inspiratory pipe 6. Fresh gas passes through the vaporisation chamber 10 where it mixes with the agent vapour 14. The resultant gas/agent mixture is administered to the patient via the unidirectional inspiratory valve 25 and inspiratory limb 6 of the breathing circuit 2 and the breathing mask 4. The patient breathes the gas/agent mixture into their lungs which dissolve some of the agent vapour 14 into the patient's blood. This leads to a reversible state of anaesthesia.

Upon exhalation by the patient, the expiratory valve 26 opens and the inspiratory valve 25 closes. The gases exhaled by the patient, including the portion of the agent vapour 14 that is not absorbed by the patient, flow back into the breathing circuit 2 via the expiratory tube 8. The exhaled gases flow into the breathing bag 28 and excess waste gas 38 is vented via the pressure-relief valve 32. A waste pipe 40 guides the vented waste gas 38 from the breathing circuit 2.

The vented waste gas 38 will contain at least trace amounts of unused anaesthetic agent vapour 14. Even trace amounts of anaesthetic in the air in a medical environment will have an effect on medical staff, continued exposure to which will cause adverse health conditions, such as headache, increased incidence of spontaneous abortion, congenital anomalies in babies and haematological malignancy. Accordingly, governmental agencies have set limits on the level of volatile anaesthetic agent that hospital staff may be exposed to. In the USA the level of volatile anaesthetic agent in the air of an operating theatre should not exceed 2 parts per million (ppm), and the level of $N_2O$ should not exceed 25 ppm. The limit set for volatile agent in the UK is 50 ppm, and for $N_2O$ the limit is set at 100 ppm.

In order to ensure that the environment within operating theatres and other medical environments stay within the above limits, the waste gas 38 which contains volatile anaesthetic agent vapour 14 is prevented from entering the atmosphere of medical environments.

To prevent the release of anaesthetic gases into the atmosphere of an operating theatre, in most developed countries, the waste gas 38 is "scavenged". In hospitals and large veterinary practices, operating theatre suites are provided with a negative pressure circuit. The negative pressure circuit is connected to the exhaust pipe 40 of the anaesthetic machine. The negative pressure circuit extracts the waste gas 38 to the atmosphere via an output pipe at the top of the building. Anaesthetic users of smaller practices extract waste gas 38 from the exhaust pipe 40 using the circuit pressure following the variable pressure release valve 32, which is at a pressure lower than the breathing circuit, to pass waste gases 38 from the exhaust pipe 40 through activated charcoal canisters. Such charcoal canisters are typically able to absorb twelve hours of waste gas 38.

However, a problem with charcoal canisters is that once they have been used they cannot be recycled and must be disposed of, which is costly.

Furthermore, unused volatile agent captured by the activated charcoal canisters may be slowly released after disposal. Volatile anaesthetic agents are halogenated fluorocarbons, and therefore their release directly into the atmosphere is particularly undesirable. Halocarbons containing bromine and chlorine groups, collectively referred to as chloroflouorocarbons (CFCs), exert a damaging effect on the ozone layer. Indeed, the release of CFCs from any industry is damaging to the ozone layer. In the stratosphere, light at higher wavelength breaks down the C—Cl/Br bond of CFCs which releases highly reactive free radical groups that break down ozone ($O_3$), depleting the earth's UV protective barrier. Isoflurane and halothane are both CFCs. Each agent has a different reactivity due to the amount of free radical each agent releases, and the ease with which the carbon-halide group is broken.

Halothane is the most reactive, due to the relative ease with which the Br group may be removed from the molecule, followed by isoflurane. Nitrous oxide ($N_2O$) also has some ozone depleting potential.

In addition, $N_2O$ and all agents, including sevoflurane and desflurane, are potent greenhouse gases due to their ability to absorb infrared light. Desflurane is the most potent due to its long atmospheric half-life. One kilo of Desflurane is equivalent to approximately 2000-3500 kg of $CO_2$.

The use of CFCs was curbed by the Montreal agreement in 1987 (and subsequent amendments). As a result, the use of CFCs in refrigeration and aerosols was banned and all CFC use not deemed 'essential' was monitored. Medical uses of CFCs are deemed 'essential' and are therefore unmonitored.

With the banning of the use of CFCs in refrigeration and aerosols, the proportion of halocarbons released into the atmosphere due to medical use has increased and is likely to increase further. Currently, forty million anaesthetics are delivered per year in the US, and five million are delivered per year in the UK. The majority of these anaesthetics are delivered under the influence of volatile agents. In addition, it is estimated that medical use of $N_2O$ contributes 3% of US $N_2O$ emissions.

An alternative way to capture the agent vapour 14 from the waste gas 38 of the breathing circuit 2 is to subject the waste gas 38 to extreme cold using liquid oxygen. Halocarbons will crystallise at around −118°. However, due to safety issues surrounding the use of liquid oxygen and the practicalities of removing and separating crystalline volatile agents from super-cold oxygen pipework, this is not a viable option for most medical establishments.

Another prior art system to capture volatile anaesthetic agent from the waste gas 38 is to pass the waste gas 38 over silicon dioxide ($SiO_2$), also known as "silica" for extraction by steam. An example of this type of prior art system is described in International Patent Application Publication No. WO 2011/026230 A1.

Similarly to the charcoal method described above, the waste gas 38 is captured from the exhaust pipe 40 and passed through canisters that contain granular $SiO_2$ to which the agent 12 binds. Once the $SiO_2$ is saturated with agent 12, the $SiO_2$ canisters are removed for processing. During processing the $SiO_2$ is subjected to a steam or nitrogen purge gas at high pressure and high temperature to separate the agent 12 from the $SiO_2$. Collected anaesthetic agent must be purified to remove water and then separated by fractional distillation.

The applicant's published International Patent Application No. WO2016/02797, hereinafter referred to as P34906WO and the contents of which are incorporated herein by reference, details methods and systems for the capture and remanufacture of halocarbons and anaesthetic agents. In this method, halocarbons are captured onto a filter material contained in a pressure-tolerant canister from the exhaust of the anaesthetic machine, then extracted and purified by chromatography and fractional separation using supercritical fluids, preferably carbon dioxide. Filter materials include Silica (SiO2), zeolites, carbon and modified or unmodified silica-based or cellulosic aerogels.

DESCRIPTION

The present invention relates to improvements to the process detailed in P34906WO with the aim of increasing process capacity, reducing $CO_2$ consumption, using low-cost materials and extracting as much halocarbon anaesthetic as possible.

Canisters tolerant to the pressures required for supercritical fluid extraction are expensive to manufacture. Pressure tolerance is only required for supercritical fluid extraction of anaesthetic agent and not for capture. An aspect of this invention specifies the use of a pressure-intolerant sleeve containing the filter material for use in the capture phase. This sleeve is then removed when anaesthetic agent breaks through the filter material and is inserted into a pressure-tolerant housing for the supercritical extraction phase.

An aspect of the present invention provides an anaesthetic halocarbon capture system for the purpose of anaesthetic halobcarbon remanufacture, comprising a pressure-intolerant sleeve containing filter material for capturing one or more types of anaesthetic halocarbon prior to supercritical fluid extraction, and a pressure-tolerant housing into which the sleeve can be inserted so as to permit exposure of the sleeve contents to pressures required for supercritical fluid extraction.

The sleeve may have a cap at either end, mobile on a seal that is capable of moving when pressurised to engage and seal the sleeve into a moulding in the pressure-tolerant extraction chamber to ensure that flow of supercritical fluid only proceeds internally through the sleeve.

A further aspect provides a method of capturing anaesthetic halocarbons comprising the steps of: providing a pressure-intolerant sleeve containing filter material for capturing one or more types of anaesthetic halocarbon; providing a pressure-tolerant housing into which the sleeve can be inserted; capturing halocarbons in the sleeve; inserting the sleeve into the housing, before during or after halocarbon capture; introducing a fluid into the sleeve; and subjecting the sleeve to temperature and pressure above the critical temperature and pressure of the fluid so as to cause extraction of halocarbons from the filter material by supercritical fluid.

The collection of anaesthetic halocarbons into pressure-tolerant canisters as in P34906WO or into pressure-intolerant sleeves containing filter material may occur from the exhaust of all different types of anaesthetic circuit, including Mapleson circuits and anaesthetic reflector systems. Collection may occur from a single or multiple anaesthetic machines.

A further aspect provides a method of extracting anaesthetic halocarbons captured onto a filter material in supercritical carbon dioxide, the system using a gas-liquid separator, comprised of cyclonic and inertial condensation methods, cooled to negative temperatures of −10 to −50 degrees Celsius to separate liquid anaesthetic halocarbon from gaseous $CO_2$.

The system may be cooled to −10 to −30 degrees Celsius

A further aspect provides a method of carbon dioxide conservation whereby gaseous $CO_2$ is recompressed after separation of the liquid anaesthetic halocarbon and re-used for supercritical fluid extraction or for supercritical fluid chromatography.

A further aspect provides a method of remanufacturing anaesthetic halocarbons from a medical environment whereby anaesthetic halocarbon captured onto a filter material in a pressure intolerant sleeve or a pressure tolerant canister is extracted using supercritical fluids in a mobile or satellite facility with transport of the fluid to a central processing facility for purification and or quality control assessment.

A further aspect provides a capture container for capturing halocarbons, the container comprising a pressure-intolerant sleeve containing filter material for capturing halocarbons prior to supercritical fluid extraction.

A further aspect provides a capture system for capturing halocarbons, the system comprising a pressure-intolerant sleeve containing filter material for capturing halocarbons prior to supercritical fluid extraction, and a pressure-tolerant housing into which the sleeve can be inserted so as to permit exposure of the sleeve contents to pressures required for supercritical fluid extraction.

In further aspects and embodiments, anaesthetic halocarbons can be captured onto a filter material in a pressure-intolerant chamber and then the filter material transferred to a pressure-tolerant vessel for the purpose of extraction of anaesthetic halocarbons.

The pressure-intolerant chamber may have a gas ingress and egress port and may be capable of connection to the anaesthetic exhaust or source of anaesthetic halocarbons as discussed in this application.

The chamber may be capable of opening, either through one of the gas ports, a further port or by the chamber being capable of being divided into two pieces, by screw thread.

The pressure-tolerant vessel can have a volume of 250 mL to 90 Litres, most preferably 1-5 Litres, with ports for the ingress of supercritical fluid and egress of the supercritical solution consisting of supercritical fluid, anaesthetic halocarbon and contaminants.

The vessel may be capable of opening to allow filling with filter material, either by a further port or by the use of a removable lid, such as that described in this application.

There may be used separate filling and emptying ports.

A further aspect provides a method of extracting halocarbons captured on a filter material, comprising the steps of: providing a first container including halocarbons captured on filter material; introducing a fluid into the container; subjecting the container to temperature and pressure above the critical temperature and pressure of the fluid so as to cause extraction of halocarbons from the filter material by supercritical fluid; providing a second container including halocarbons captured on filter material; and transferring supercritical fluid from the first container into the second container to drive extraction of halocarbons therefrom.

In some aspects and embodiments the sleeve comprises ingress and egress conduits that are exposed when the sleeve is placed inside the pressure-tolerant canister so that it can be incorporated into the supercritical circuit.

The advantages of this process are the reduced costs of manufacture for multiple canisters and the use of sleeve materials that do not react with anaesthetic agents or leach reactants or products under exposure to supercritical fluids.

The housing is resistant to supercritical fluid to enable captured halocarbon to be reclaimed by being dissolved in a supercritical fluid to form a supercritical solution.

The housing may be arranged to withstand fluid at supercritical pressure which may be between about 7 MPa (7.29 MPa is the critical pressure for $CO_2$) and 50 MPa; and/or may be arranged to withstand fluid at supercritical temperature which may be between 30° C. and 300° C.

The halocarbon may be a volatile anaesthetic agent.

The methods and devices of the present invention may comprise passing gas containing one or more volatile anaesthetic agents through filter material. The material may be granular silica, zeolite, carbon, activated carbon or the material may be or comprise aerogel. The most common aerogel is made of silicon dioxide ($SiO_2$), but aerogels according to the invention may be made from or comprise other materials, for example, resourcinol formaldehyde, carbon, calcium carbonate and zeolite (aluminosilicate). Zeolites are micro-porous alumina silicate minerals found naturally but may also be made artificially. Carbon may be exposed to high temperatures to expand its surface area for absorption. The filter material may be doped with a metal.

Aerogel may be functionalised by the addition of one or more of halocarbon, metal oxide, cellulose, carbon nanotubes, or internally supported by polymers to improve their chemical or mechanical properties. These changes may improve the binding of halocarbons and/or the stability of the aerogel. For example, functionalisation with halocarbon improves the binding of halocarbon to the material. The material may comprise granular particles.

Furthermore, the material may comprise or be a metal or metal oxide which may be formed by forming metal-oxygen-metal bridges. Examples of preferable metals and metal oxides include nickel, molybdenum, alumina, titania, zirconia, iron, chromia, vandia platinum, rhodium, palladium and tungsten. The material may comprise or be a precious metal. A metal and/or a metal oxide may be added by deposition to the material, for example by physical or chemical vapour phase deposition.

The sleeve may be arranged to allow the ingress and egress of gas containing halocarbon anaesthetic and/or supercritical fluid through the material. Preferably, the sleeve may comprise a first conduit to allow the ingress and egress of gas and supercritical fluid. The sleeve may comprise a second conduit to allow the ingress and egress of gas and supercritical fluid, wherein the first conduit may allow gas to ingress into the sleeve and supercritical fluid to egress the module; and the second conduit may allow gas to egress the sleeve and supercritical fluid to ingress into the sleeve. The sleeve may comprise a first pair of conduits and may comprise a second pair of conduits. Either or both pairs of conduits may be arranged to allow the ingress and egress of fluid through the filter material. Preferably, the first pair of conduits may allow the ingress and egress of gas, and the second pair of conduits may be arranged to allow the ingress and egress of supercritical fluid.

Initially the sleeve is mounted onto or nearby the anaesthetic machine or alternatively in an area that receives exhaust gas from multiple theatres. The ingress port of the sleeve is linked via an appropriate connector and pipework to the source of the anaesthetic agent and the egress port is connected to the scavenging system, charcoal filter or directly to the atmosphere via appropriate connectors.

Connectors may be made of metal or an appropriate plastic that does not leach chemicals or absorb significant amounts of anaesthetic agent. The connector may be specific to the anaesthetic agent used in that facility. This is advantageous in the remanufacture of single anaesthetic halocarbons or in the collection of anaesthetic halocarbons from veterinary and human sources The filter material in the sleeve is exposed to anaesthetic agents derived from the anaesthetic machine and/or theatre environment. Once the sleeve has been exposed to anaesthetic agent, and the filter material has absorbed/adsorbed the anaesthetic, it is removed and replaced.

The halocarbon anaesthetic may bind to the material as the gas passes through the material.

In some embodiments, the method may be performed in a medical environment, for example a hospital or veterinary facility.

The gas may be from atmospheric air in a medical environment. The gas may be supplied by an anaesthetic machine or many anaesthetic machines. The gas may be supplied by a single or multiple cardiopulmonary bypass machines. Accordingly, a further aspect of the invention extends to a method of capturing anaesthetic agent from a gas, the method comprising passing gas containing anaesthetic agent through filter material contained by containers formed in accordance with the present invention.

The invention can be used to capture anaesthetic halocarbons from different anaesthesia systems. These include but are not limited to, circles, the various semi-open systems as classified by Mapleson, reflector circuits and direct injection anaesthesia systems. The collection sleeve or pressure tolerant canister as mentioned in P34906WO can be used before the anaesthetic gas scavenging system (AGSS), charcoal canister or direct atmospheric ventilation. Furthermore it can be used to collect anaesthetic halocarbons collected from several theatres or a hospital as part of the anaesthetic gas scavenging system. The canister or sleeve may also entrain air from a medical environment in which anaesthetic halocarbons are present, such as the operating theatre, anaesthetic room or theatre recovery areas.

In another embodiment of the invention, the sleeve or the feed of anaesthetic halocarbon into the sleeve may be cooled during collection, using methods including but not limited to the use of a thermal jacket containing coolant or a Peltier cooler. Cooling improves the binding of the anaesthetic halocarbon to the filter material. This is especially relevant for Desflurane, which has a lower boiling point (23° C.) than Sevoflurane (58° C.) and Isoflurane (48° C.) and higher vapour pressure at room temperature. Pressure-swing absorption may be used to further increase capture capacity. This method refers to the intermittent application of pressure to the gaseous contents of the sleeve to increase binding affinity.

A method for increasing the amount of volatile anaesthetic halocarbon captured onto a filter material, the method comprising cooling the exhaust gas entering the canister or pressure-intolerant sleeve or cooling the canister or pressure-intolerant sleeve itself.

A method for increasing the amount of volatile anaesthetic halocarbon captured onto a filter material, the method comprising the use of cyclical pressure changes applied to the canister or sleeve, referred to as pressure-swing absorption.

According to the present invention there is also provided improvements in or relating to a method for reclaiming, removing or extracting volatile anaesthetic agents from a material. The method may comprise exposing or subjecting the filter material in a sleeve to a supercritical fluid. A supercritical fluid will expand to fill its container and effuse through solids like a gas and dissolve materials like a liquid. Subjecting material to which halocarbon is bound to a supercritical fluid breaks the interactions between the halocarbon and the material, and the halocarbon may be displaced from the material and/or dissolves in the supercritical fluid to form a supercritical solution containing the halocarbon. Accordingly, the halocarbon may be bound to or interact with the material so that when the material is exposed to supercritical fluid, the halocarbon may be displaced and dissolves in the supercritical fluid. The material may contain a plurality of different halocarbons which may be reclaimed from the material. The supercritical solution may then carry the halocarbon away from the material leaving the material intact. A supercritical fluid is a substance at a temperature and pressure above its critical point where distinct states of gas or liquid do not exist.

The supercritical fluid may be or comprise supercritical carbon dioxide ($CO_2$). Alternatively, the supercritical fluid may be or comprise nitrous oxide ($N_2O$). Carbon dioxide exists in a supercritical state above its critical temperature (31.1° C.) and critical pressure (7.39 MPa). This temperature is close to room temperature and the pressure is within pressures often used in medicine and in operating theatres. The halocarbon may be one or more anaesthetic agents which are very soluble in supercritical $CO_2$ and may be washed from the material by dissolving in supercritical $CO_2$. Other halocarbons or other contaminants may be eluted as well as anaesthetic agents. These are either from normal human metabolism (eg methanol, formaldehyde, methane, even chloroform or from breakdown of the anaesthetic agents. Sevoflurane is especially vulnerable to breakdown by dry alkali-based $CO_2$ absorbers present in the anaesthetic circuit. These chemicals include but are not limited to Hexafluoroisopropanol (HFIP), Compound A and Compound B These compounds, as they are not volatile anaesthetic agents themselves, are referred to as 'contaminants' for the purposes of this invention.

The sleeve may be placed into the pressure tolerant housing by automated means. The housing would be opened, the sleeve placed into the housing and the housing closed for subsequent extraction. After extraction, the housing would be opened, the eluted sleeve removed and new sleeve placed into the housing, before the housing is closed. A number of methods known to those familiar in the art of automation can be used to move components, control the process or provide feedback to determine task completion. The process may be under the control of a microcontroller or Programmable Logic Controller (PLC) and may output information to a managed information system for regulatory compliance.

The present invention also provides a method for the automated extraction of anaesthetic halocarbons, the method comprising the use of an automated mechanical system to open the pressure vessel, remove the previous sleeve, place a new sleeve, close the pressure vessel and control the flow of supercritical and subcritical fluids throughout the system as described in P34906WO and this invention.

The present invention also provides a method for achieving regulatory compliance in respect of the proper functioning of automated systems in the manufacture of active pharmaceutical ingredients, the method comprising controlling the automated process by the use of a Programmable Logic Controller (PLC) and the output of information from the PLC system to a persistent, managed information system to demonstrate proper system function to regulatory agencies.

The present invention also provides a method for the management of automated systems involved in the remanufacture of anaesthetic halocarbons in multiple locations around the world, whereby information regarding the function and performance of the system is transferred from the Programmable Logic Controller onto a single board computer and then passed by secure messaging system to the cloud or central server for visualization and control.

The sleeve and housing may be configured in different ways. In order for the sleeve not to take pressure, the housing may be allowed to pressurize around the sleeve by the use of a small bypass channel present in the supercritical fluid input or output end. This may be closed at the other end to prevent full bypass. However, although this protects the sleeve from taking any pressure, the exterior of the canister is exposed to the supercritical fluid and any compounds of the exterior of the canister will be exposed to supercritical fluid and may be extracted. The weak point of the sleeve is at the ends and their connection to the cylinder.

Therefore, in a further embodiment of this invention, the sleeve is made of a pressure tolerant cylinder with floating ends, sealed to the cylinder by seals. The ends have single or dual ingress/egress ports that connect to the source of the anaesthetic agent and fit inside the moulded ends of the pressure-tolerant housing. When the sleeve is placed into the pressure vessel and pressurized, the ends move outwards slightly, sealing the ends of the sleeve to the moulded ends of the pressure-tolerant housing. In a preferred embodiment the lid of the housing is connected to the body of the housing by a bayonet fitting although other mechanisms such as screw or pressure-hold or other may be used as known to those familiar in the art. With this sleeve form, the ends are supported by an appropriately shaped housing lid that takes the pressure of the supercritical fluid. The cylinder is tolerant to supercritical pressures but may not have a factor of safety consistent with safety according to the pressure vessel safety directive or other such document, but may be supported by the walls of the housing and is contained in the pressure vessel to maintain safety. In this way, the supercritical fluid is not exposed to the outer wall of the sleeve.

It is anticipated that other methods of configuring the sleeve and housing would be possible to achieve the same goals. For example this could include a separate pressure supply for the external aspect of the sleeve, balanced to the internal pressure and vented upon housing depressurization. This is not used as it involves the loss of $CO_2$ from the system.

A further aspect of the invention condenses the anaesthetic halocarbons from the supercritical solution before chromatography and removes carbon dioxide. P34906WO claims the use of a cooled cyclonic collector for condensation of halocarbons from a supercritical solution. In this aspect of the invention, cooled cyclonic collection is combined with inertial condensation in the same module and operates at low pressures of 1-20 bar.

Volatile anaesthetic agents exist as a liquid with vapour phase at room temperature. In order to separate liquid volatile anaesthetic agent from gaseous $CO_2$ the vapour pressure of the anaesthetic agent must be reduced to at or near zero. In order to reduce the vapour pressure of the anaesthetic agent, the temperature must be reduced. For example, our experiments have demonstrated that Sevoflurane and Isoflurane have a negligible vapour pressure below −20 degrees Celcius. However, at these temperatures, carbon dioxide will be a liquid at lower pressures than those it operates at when supercritical. In an aspect of this invention, the supercritical solution is passed into a gas-liquid separator. This is encased in an external thermal jacket that is supplied with cold fluid (eg Polyethylene Glycol) at −20 degrees Celcius. The cyclonic collector has a series of eccentric injection points of a narrow aperture that form a cyclonic flow of gas around a cone, ejecting liquid halocarbon to the cooled side walls. The chamber volume increases as the gas passes down the cone, the gas velocity slows and the gas passes through a layer of beads, cooled in the chamber. Liquid halocarbon that has not formed droplets of sufficient size to be removed by the cyclone impacts the beads and condenses. The beads also serve to protect the condensed anaesthetic halocarbon from the flow of gas through the gas-liquid separator. In order to maximize the cooling, the supercritical solution is depressurized immediately adjacent to and within the gas-liquid separator. The solution is reduced from supercritical pressures (above 73 bar) to low pressures (2-20 bar) in the gas-liquid separator, although the input pressure may be reduced prior to the reduction in/near the gas liquid separator The adiabatic expansion of the supercritical fluid reduces the temperature in the gas-liquid separator to −20 to −40 degrees Centigrade depending on the flow rate of the supercritical solution. The aim of the temperature/pressure combinations is to ensure the $CO_2$ can depressurize to a gas at negative temperatures that reduce the vapour pressure of the anaesthetic halocarbon to near zero. Some advantage in flow rate is gained by the $CO_2$ leaving the gas-liquid separator at sufficient pressure to supply a gas-booster that increases the pressure of the $CO_2$ back up to supercritical pressures for resupply to extract further anaesthetic. However, atmospheric pressure $CO_2$ from the gas liquid separator can be passed through a large single-stage or double-stage gas booster to achieve the same flow rates. As the $CO_2$ is pressurized, it is heated above 31 degrees Celsius and therefore enters a supercritical state ready for extraction. In this way, a loop is established to conserve $CO_2$ and allow any uncondensed anaesthetic halocarbon to pass back through the gas-liquid separator. Further heating can be supplied in the temperature controlled environment used for extraction.

In a further aspect of the invention, the liquid that exits the gas liquid separator is separated from dissolved $CO_2$. As the gas-liquid separator operates at 1-20 bar, an amount of $CO_2$ proportionate to the partial pressure is dissolved in the liquid anaesthetic agent. This is increased at the low temperatures of the gas liquid separator. Therefore, the liquid is passed into a collection chamber with a thermal jacket and separated from the gas liquid separator by a valve. When the valve is actuated to separate the collection vessel from the extraction circuit, the pressure of the vessel is allowed to reduce to atmospheric pressure gradually through a flow-restrictor while the temperature of the collection chamber is maintained at a level that gives a near zero vapour pressure of the anaesthetic halocarbon. Once the vessel is depressurized, it is warmed gradually and any further dissolved $CO_2$ released via a reflux condenser operating at −20 to −30 degrees Celsius. Any released gas is passed back to a gas booster, repressurised and fed back into the extraction process to conserve $CO_2$ and anaesthetic agent. This process can operate at the same time or separately from the extraction of anaesthetic agent depending on the number and size of collection chambers. The size may vary from 50 mL to a full batch size of up to 90 Liters, although other sizes less than or in excess of this may be used. Water may be added to Sevoflurane in small amounts (150-300 ppm) to prevent lewis acid breakdown.

The purpose of condensation of the anaesthetic halocarbon and any contaminants that also dissolve in supercritical $CO_2$ at this stage is to concentrate the anaesthetic before chromatography but also to form a batch for subsequent processing. Due to the regulatory requirements, it may be preferable to determine the contents of the material before chromatography. Therefore, extraction can be followed by condensation and quality control assessment before purification by chromatography is started.

A further aspect of the invention increases the concentration of anaesthetic agent in the supercritical fluid before chromatography. Supercritical fluid chromatography enables the separation of anaesthetic agents from contaminants and each other. This is required for regulatory approval and resupply to the consumer. Column charge volume and concentration determine the processing flow of the column but also affect the ability of the column to resolve individual compounds. It is important to note that it is not necessary to condense the anaesthetic halocarbon at this stage for the process to work and therefore, the process can be viewed as a single entity from start of extraction to completion of purification, driven by supercritical fluid. However, breaks in the process may be used for the purposes of regulatory compliance or due to process/workflow optimization.

In another aspect of the invention, $CO_2$ is conserved by the use of multiple extraction housings. This may refer to the pressure tolerant canisters in P34906WO or the pressure vessels and sleeves in this invention. The volume of carbon dioxide at room temperature and pressure required to pressurize such a housing volume above critical pressure is very large. This volume of carbon dioxide would be lost to the atmosphere on depressurization when the canister is removed.

Elution of anaesthetic halocarbon during extraction rapidly reaches a peak and declines in an exponential manner. Elution will not complete to 100% as this would take too much time. Therefore on depressurization and removal of the canister, if vented to atmosphere, a significant quantity of anaesthetic agent would be lost.

The present invention specifies an improvement to the depressurization system in P34906WO. In the present invention, when it is decided that the extraction phase has completed, the carbon dioxide and remaining anaesthetic agent from the first housing/sleeve is pumped into another housing/sleeve. This will bring the next housing/sleeve up to above critical pressure. Following this, supercritical carbon dioxide can be introduced to the second housing/sleeve to drive extraction of captured anaesthetic agent for subsequent condensation and supercritical chromatography. In a preferred embodiment, extraction housings operate in sets of 3. At a single timepoint, one housing/sleeve is being subjected to the flow of supercritical fluid and the anaesthetic halocarbon extracted whilst another housing/sleeve that has just finished extraction but is still pressurized has its contents ($CO_2$ and anaesthetic halocarbon) transferred to another housing/sleeve which has yet to be extracted. At the end of this process, the first referred to housing/sleeve has finished its extraction, the second housing/sleeve is at atmospheric pressure and can be opened and the sleeve removed and replaced, and the third housing/sleeve is pressurized and ready for extraction to begin. Following this timepoint, the sleeve in the second housing is replaced and the first housing/sleeve contents are transferred into the second housing/sleeve while the third housing is subjected to the flow of supercritical fluid and its anaesthetic halocarbon extracted.

In a preferable embodiment of the invention, the transfer of the supercritical solution from one donor housing/sleeve to the recipient housing/sleeve would proceed as follows:

1. Initially down the pressure gradient between the two chambers.
2. By pumping of the remaining gaseous contents of the donor housing/sleeve into the recipient housing/sleeve. In a preferred embodiment, this would use a commercially available gas booster pump, operating from a pressurised air supply. However electric pumps or turbine-driven systems could also be used.

By this method, continuous extraction can proceed and $CO_2$ and anaesthetic halocarbon are conserved.

It is anticipated that other similar methods may be used to achieve these goals as known to those familiar in the art.

In a preferred embodiment of the invention, depressurized anaesthetic halocarbon is passed through a 40 micron and then a 15 micron filter before storage. These filters are intended to remove particulate and infective (bacterial, viral and prion-related) before further purification. Additional sterilization steps that do not breakdown the anaesthetic agent may be used at this or any other stage as required by the regulatory agencies. These techniques are well known to those skilled in the art of pharmaceutical production, and may include but are not limited to heat and/or pressure UV or ionizing radiation.

The sleeve, the housing, gas-liquid separator, collection and storage vessels and other materials that contact the supercritical solution may be manufactured from stainless steel or aluminium with or without a polymer coating to prevent anaesthetic agent breakdown. Polymer coatings may include but are not limited to Polytetrafluoroethylene (PTFE), Polyimide and Polyethylene Napthalate (PEN). Sleeve endings may be formed spinning, extrusion, injection, impact moulding or printed although other common manufacturing techniques are not excluded.

In the circumstances below, the purity of the anaesthetic halocarbon recovered after its extraction by supercritical fluids may be sufficient to be returned to the consumer without further chromatographic purification.
1. Single anaesthetic agent source
2. No anaesthetic breakdown products produced:
    a. Isoflurane or Desflurane
    b. Sevoflurane without $CO_2$ absorber or using a $CO_2$ absorber that does not breakdown sevoflurane (such as Amsorb).

P34906WO details an anaesthetic machine capable of recycling anaesthetic halocarbons and delivering them directly back into the anaesthetic machine. If the conditions in 2 above are met, then this system may not chromatographic purification after extraction. The selection properties of the filter material and supercritical $CO_2$ are capable of purifying the anaesthetic halocarbon sufficiently.

A method for the recirculation of anaesthetic within an anaesthetic machine for resupply to the patient, whereby:
  exhaled anaesthetic halocarbon not recirculated through CO2 absorber is captured onto a filter material in a pressure-tolerant housing
  two pressure-tolerant housings are present, one to capture anaesthetic halocarbons and one to undergo extraction using supercritical fluid, the function of each rotating after the filter material has captured sufficient anaesthetic halocarbon
  the filter material is exposed to supercritical fluid, preferably carbon dioxide, and the anaesthetic halocarbon extracted
  the extracted anaesthetic halocarbon is condensed and separated from most of the gaseous $CO_2$ at subcritical pressures
  the anaesthetic halocarbon is returned into the breathing circuit of the anaesthetic machine (circle, mapleson, reflector) to conserve anaesthetic agent.
  any remaining $CO_2$ is absorbed by the $CO_2$ absorber.

The costs of transporting canisters with captured anaesthetic can be reduced by using remote extraction equipment. This can take three forms:
1. A mobile service in which the equipment is contained within a vehicle
2. An individual extraction unit installed in the client facility
3. A centralised, joined, collection and extraction system It is envisaged that I will be used for small consumers (eg. Veterinary practices and small hospitals) and 2 or 3 will be used for very large consumers (eg. tertiary/quaternary hospitals or in cities/regional extraction centres In these systems, sleeves are filled with anaesthetic agent by the client. In the mobile service, the extraction system as detailed above is contained in a vehicle. Sleeves are loaded into the pressure containers and the contents extracted, condensed and separated from the $CO_2$, with the $CO_2$ recycled as described previously. The sleeves are then returned to the client and the liquid is transported back to a processing facility for chromatography purification, bottling and quality control. Anaesethetic agents may be collected individually or mixed (combinations of sevoflurane, isoflurane and desflurane).

In a separate embodiment of the invention, the extraction system could be contained in a unit installed in the client's facility. In large hospitals, this will reduce the number of sleeves required and transport costs. Sleeves are filled with anaesthetic agent and loaded into a rack that automatically loads the capture sleeve into pressure-tolerant housings to extract, condense, separate and recycle $CO_2$ as described above. Sleeves are then stored to be taken back to the machines and the liquid anaesthetic agents are stored for subsequent collection and transfer to a facility for purification, bottling and quality control.

In another embodiment as referred to in P34906WO, anaesthetic gases from multiple theatres can be collected onto the filter material of a pressure-tolerant chamber. These large central, pressure tolerant chambers containing the filter material are connected to the Anaesthetic Gas Scavenging System collecting from multiple theatres. These chambers have an ingress and egress port for the flow of gas from the scavenging system and ingress and egress ports for the transfer of supercritical fluids, preferably carbon dioxide. These ports may be separate or shared as collection and elution occur independently. Two pressure tolerant chambers would operate together. One chamber is set to collect anaesthetic exhaust gases and the next chamber is set for extraction. When full, as detected by weight change, infrared or photoacoustic gas analysis, the chamber ingress and egress ports for exhaust gases are closed and the system is pressurised up to supercritical pressures and warmed to supercritical temperatures by the passage of $CO_2$ warmed over 31 degrees Celsius. Extraction, condensation, separation and $CO_2$ recycling then proceed as described above. The liquid anaesthetic agents are collected and transferred to a facility for purification, bottling and quality control. These remote systems may be managed centrally by the transfer of information to and from the Programmable Logic Controller to a central server or cloud-based information system.

Liquid $CO_2$ below supercritical temperatures can be used to extract anaesthetic agents. The performance of this is not an improvement on the supercritical process, as the higher temperature improves the desorption of anaesthetic halocarbons and therefore reduces the time taken to extract the anaesthetic halocarbons from the filter material.

P34906WO specifies the use of chromatography columns in series to separate agents using supercritical fluid chromatography, preferably supercritical $CO_2$. The first column separates out hydrophilic contaminants commonly exhaled in breath (such as methanol, ethanol, formaldehyde etc) from halocarbon based on polarity (dipole and hydrogen bonding). In one aspect of this invention the stationary phase in the first column would be a cyano-modified silica gel, although other columns including but not limited to 4-Ethylpyridine, 2-Ethylpyridine and C-18 columns could be used.

The second column specified in P34906WO is based on size-exclusion chromatography to separate different anaesthetic agents from each other. In another aspect of this invention, a DEAP (Di-ethyl-aminopyrindine) column may be used to separate different anaesthetic halocarbons from other halogenated contaminants (such as HFIP, Compound A/B etc). This has separation effects by size exclusion, preferably 5-120 Angstrom pore size, most preferably 40-60 Angstrom pore size. The DEAP stationary phase may also have polarity-based effects. This may occur with or without the use of a modifier such as methanol or ethanol, although other modifiers may be used by those skilled in the art. Modifier may be used in concentrations of 0 to 50%, most preferably 10-20% although other concentrations may be used.

Supercritical fluid chromatography, with or without modifier, is used to separate halogenated contaminants from the halogenated anaesthetic agents using size-exclusion or polarity-based chromatography or a combination of both methods. Most preferably, this would use a Diethylaminopyridine chromatography column.

A further aspect of the present invention provides a method for separating one or more halocarbons from a supercritical solution, the method comprising a polarity-based separation step to separate out contaminants and/or to separate out one or more different types of halocarbon.

A plurality of polarity-based separation steps may be used.

Modifier such as methanol or ethanol may be used to improve separation of anesthetic halocarbons or contaminants with similar polarity or size-charge configurations.

At least one separation step may be used to separate contaminants and the or at least one of the further steps is used to separate out one or more different types of halocarbon.

One or more separating columns may be provided. For example a plurality of columns arranged in series may be provided.

The present invention also provides an anaesthetic agent collection system for fractionally separating one or more anaesthetic agents from agent-product in a supercritical state, the system comprising one or more chromatography columns which intermittently deliver anaesthetic agent dissolved in supercritical fluid to one or more fractionation columns, the system further comprising an expansion chamber for buffering the intermittent flow of agent from the chromatography columns whereby to generate a substantially continuous flow for the fractionation column/s.

The present invention also provides a recirculation system for separating individual anaesthetic agents by supercritical fractionation, the system including a plurality of separating columns arranged in parallel.

The present invention also provides an atmosphere scrubbing device comprising a halocarbon capture medium.

The present invention also provides an atmosphere scrubbing device comprising a capture medium for capturing one or more types of environmental pollutant.

The capture medium may be an aerogel. The aerogel may be based on cellulose and modified by a halocarbon.

The present invention also provides a device as described herein carried on or by, or forming part of: a building; an aeroplane, a balloon. This may be used, for example as part of a large-scale atmosphere filtering processing in a city.

The present invention also provides a method for the safe breakdown of nitrous oxide and its intermediates by dilution in supercritical carbon dioxide at temperatures and pressures to create a mixture of supercritical fluids.

The breakdown of supercritical nitrous oxide diluted in supercritical carbon dioxide may be catalysed by a catalyst, preferably a precious metal such as platinum, rhodium, palladium or a transition metal oxide such as but not exclusively limited to chromia or aluminia.

The reaction may require a further reactant: urea, ammonia or anhydrous ammonia.

The catalyst may be bound to the filter material and reactant added to the capture chamber.

The catalyst may be bound to a material, such as but not exclusively limited to a ceramic or aerogel, and is reacted with supercritical nitrous oxide diluted in supercritical carbon dioxide and urea or ammonia in a separate chamber subsequent to the capture chamber.

The present invention also provides a method for separating one or more halocarbons from a plurality of halocarbons dissolved in a supercritical solution, the method comprising supercritical chromatography using a polarity-based column.

Supercritical fluid chromatography may also separate the different anaesthetic halocarbons from each other. This separation may require the use of a modifier such as methanol or ethanol, although other modifiers may be used by those skilled in the art. In one aspect of this invention, a DEAP column with the use of a modifier in concentrations of 0-50%, most preferably 20%, and supercritical $CO_2$ is used to separate Sevoflurane from Isoflurane. Desflurane may also be separated from Sevoflurane and Isoflurane or may be separated by fractional distillation as the boiling point of desflurane is significantly different than Sevoflurane or Isoflurane. In another aspect of this invention, water can be added to the modifier in small amounts 0-5%, with ethanol or methanol at 0-50% to improve the separation. Ideally, non-toxic or low-toxicity modifiers are used, such as ethanol and water.

Supercritical fluid chromatography, preferably using $CO_2$ as the supercritical fluid, can be used with or without the presence of modifier to separate different anaesthetic halocarbons from each other using a size-exclusion and or polarity based column, most preferably a Diethylaminopyridine column. The modifier may be ethanol, water, methanol, a mixture of these or other modifiers know to those skilled in the art.

Anaesthetic halocarbons leaving the top of the chromatography columns are detected by Infrared (IR) spectroscopy using a flow cell with a small volume, preferably of 1-1000 microliters, most preferably 10-50 microliters, clamped to a diamond Attenuated Total Reflection (ATR) lens. The lens allows micrometer penetration into the sample and the use of such a small pressurized chamber to give temporal resolution required for column control. If required, multiple IR images can be taken over time to give spectrum resolution to positively identify the anaesthetic halocarbons by their infrared signature. Other monitoring technologies including but not limited to mass spectrometry, UV and raman spectroscopy may be used in place of IR spectroscopy.

Infrared detection of anaesthetic halocarbons using a diamond ATR lens, preferably with a volume of 1-1000 microlitres, most preferably 10-50 microliters can be used to control the path of compounds leaving the chromatography columns.

Anaesthetic halocarbons that have been extracted are loaded onto the columns by loading a known volume loop of pressure-tolerant tubing with the anaesthetic halocarbon and then, under microcontroller control, the loop is introduced into the flow of the supercritical fluid, entering the column for separation. The volume of injection may vary, preferably in the range 1-50 mL although higher volumes can be used. Two different columns may be required to separate hydrophilic contaminants (relative to the halocarbons) from the anaesthetic halocarbons and subsequently halocarbon contaminants from the anaesthetic halocarbons and separate anaesthetic agents depending on the composition of the extracted product. Multiple parallel banks of these columns in series can be used to increase the capacity of the system.

The anaesthetic halocarbons exit the column early due to minimal interaction with the stationary phase of the column. Contaminants in each column are retarded compared to the anaesthetic halocarbons.

In the separation of contaminants from the anaesthetic agents, chromatography retention times are very short for the anaesthetic agents due to their high solubility in the mobile phase (supercritical $CO_2$). Retention times for contaminants such as ethanol, methanol, formaldehyde, acetone etc. are much longer in polar columns (eg. Cyano, C-18, 2-Eythyl Pyridine). Following the elution of the anaesthetic agent fraction, flow can be reversed in the column and the rate increased. The contaminants that have not passed far up the column have their flow reversed and are eluted from the bottom of the column for waste. In this way the column is rapidly cleaned for the next injection.

A method for improving the production capacity of supercritical fluid chromatography for the purification of anaesthetic halocarbons for resupply to the consumer, the method comprising using reverse flows of the supercritical fluid to flush higher-affinity contaminants from the chromatography column following the elution of the anaesthetic halocarbon.

In an alternative embodiment, this invention describes the use of pressure-swing chromatography to assist purification. By this method, the back-pressure regulator which maintains the pressure in the systems above the critical pressure of $CO_2$, applies a variable supercritical pressure on a cyclical basis to the chromatography system. Higher pressures increase absorption of the anaesthetic agents and contaminants to the stationary phase. Lower pressures cause desorption of the compounds. The rate of absorption and desorption depends on the affinity of the molecule to the stationary phase. Molecules with a higher affinity increase their absorption more rapidly and desorb more slowly. Therefore, their progress through the column is slowed more than low-affinity compounds. Anaesthetic agents are very soluble in $CO_2$ and therefore do not interact much with the stationary phase. Therefore, their progress through the column is not much altered by pressure-swing chromatography. Contaminants have a stronger affinity for the stationary phase than the anaesthetic halocarbons and therefore their progress is significantly reduced by pressure-swing chromatography. By using this method, the elution peak resolution can be improved and therefore columns can be loaded with a higher volume and concentration, improving the throughput of anaesthetic agent through the purification process.

Pressure-swing chromatography may be used to improve separation of anaesthetic halocarbons from contaminants and each other.

Multiple injections may be made onto a single separation column before the anaesthetic halocarbon has eluted from the column to improve system flow capacity.

Experiments have shown that a long column length is required to achieve separation. Multiple injections can be made onto the column. However, this is still a batch process. This can be made into a continuous process by the use of simulated-bed moving chromatography. The use of this process enables the effective column length to be increased indefinitely (it is a circular system) using fewer columns and higher throughput by using a continuous process, reducing the costs and $CO_2$ consumption. In this process, valves are used to change the position of the column feed inlet, solvent inlet and desired product exits and undesired product exit. The system operates best for the separation of a small number of molecules. Therefore this is best suited to the separation of anaesthetic halocarbons from each other after initial removal of contaminants has taken place.

Although it is possible and claimed to separate all three agents and contaminants in one process, we will most often operate the separation of two agents and contaminants. Our batches contain a mixture of two agents or are single agent due to the way that anaesthetic agents are used in the clinical environment, which is beyond the scope of this application. The mixtures are Sevoflurane and Desflurane, Sevoflurane and Isoflurane or Isoflurane and Desflurane. Therefore this application claims the separation of each of these mixtures and contaminant, a mixture of all three agents and contaminant and each agent individually and contaminant.

Once anaesthetic halocarbon exits the chromatography column they are directed to collection. This may be specific to the anaesthetic agent. Methods of direction may include but are not limited to the use of rotary or high pressure solenoid valves. The anaesthetic halocarbon, mixed with $CO_2$ is fed to a gas-liquid separator as described previously. This consists of a continuous loop of recirculating $CO_2$ to ensure that $CO_2$ is not wasted and any anaesthetic not condensed in the separator will pass through the gas liquid separator again. Liquid is collected and any further $CO_2$ released by gradual depressurization (with $CO_2$ returned to the condensation loop) and warming with anaesthetic halocarbon retained by a reflux condenser as described previously.

According to another aspect of the invention, there is provided a method for the use of higher pressures than in P34906WO that may require the fractionation columns to be warmed to selectively condense less volatile agents. Higher pressures, preferably 5-60 bar although other sub-critical pressures may be used, reduce the column flow rates to improve column thermal stability and gas transit time but require the first column to be heated to prevent the condensation of the second anaesthetic agent.

In a preferred embodiment of this invention an expansion chamber is incorporated into the circuit 600a as described in P34906WO. This expansion chamber receives a feed of subcritical $CO_2$ that has been depressurized by a variable pressure-reducing valve from the accumulator and also receives the charge of anaesthetic agent and $CO_2$ from the chromatography back pressure regulator. The expansion vessel allows a continuous flow of sub-critical pressurised $CO_2$ through the columns to develop and maintain thermal stability. Aliquots of anaesthetic agent dissolved in super-critical $CO_2$ are delivered from multiple chromatography columns after selection by infrared spectroscopy and depressurized by a back pressure regulator into the expansion chamber. This delivery is intermittent, whereas the fractionation columns require a continuous flow of $CO_2$ to maintain efficiency. The expansion vessel uses the direct feed of $CO_2$ from the accumulator and its own volume to buffer the intermittent delivery of anaesthetic agent from the chromatography columns to generate a continuous flow for the fractionation columns.

According to a further aspect of this invention a process is described whereby a recirculation system to separate individual anaesthetic agents by supercritical fractionation operates by using columns in parallel rather than in series as in process patent P34906WO. In this system, a plurality of purified anaesthetic agents dissolved in $CO_2$ is delivered in bursts from the chromatography-based purification system as the anaesthetic agents are selected from contaminants under infrared or other detection means. It is depressurized below critical pressure by the back-pressure regulator leading to a gaseous state but is maintained at pressure, preferably 2-10 bar although other sub-critical pressures may be used. This charge of gas passes into an expansion chamber in a temperature-controlled environment that mixes it with fresh and re-circulated $CO_2$ and equilibrates temperature. The gaseous mixture passes into a fractionation column that due to the pressure of the mixture may require heating, preferably from 0 to 300 degrees Centigrade, to allow condensation of the less volatile agent but leave the $CO_2$ and more volatile agent in a gaseous form to pass through the column. It is anticipated that this column will not be 100% efficient. It is intended to ensure that only a single agent is condensed, but this is at the expense that not all of the less volatile agent is collected on the first pass. Remaining gases are then recirculated to the expansion vessel and pass through the column again multiple times. In this way, the entire less volatile agent is condensed over several passes with the more volatile agent and $CO_2$ remaining in a gaseous state. Once infra-red spectroscopy detects that only the more volatile agent remains, it signals to a controller to switch a valve and pass the gases from the expansion chamber into a different column which is held at pressure of 2-10 bar, although other sub-critical pressures may be used in a cooled environment of −30 to −20 degrees Celsius. This ensures that $CO_2$ remains gaseous but that the more volatile anaesthetic agent condenses for collection. Further re-circulation cycles ensure that all of the more volatile agent is condensed and only pure $CO_2$ remains before the process is stopped and the pure $CO_2$ is stored for re-use.

The condensed anaesthetic agents are allowed to leave the pressurised fractionation columns by computer-controlled needle valves that pass the separated liquid anaesthetic agents into a temperature controlled expansion vessel. The vessel fills with liquid anaesthetic agent at or near atmospheric pressure but is sealed and its internal volume increases to maintain atmospheric pressure. Carbon dioxide will be dissolved into the anaesthetic agent at the partial pressure it was in the column. This $CO_2$ will be released as a gas as the anaesthetic agent is depressurized, vapourising some anaesthetic agent. The expansion vessel will therefore be cooled to condense all the separated anaesthetic agent but leave the $CO_2$ in its gaseous state. Carbon dioxide will then be released and the liquid anaesthetic agent removed, bottled and warmed to room temperature after passing through a quality control check using gas chromatography-mass spectrometry to ensure purity.

According to a further aspect of this invention a process is described whereby a recirculation system to separate individual anaesthetic halocarbons operates by warming the gas liquid separator. This process is driven by the use of $CO_2$ that has been depressurized from supercritical state. In patent P34906WO, this is referred to as 'supercritical fractionation' although it occurs at subcritical pressures and temperatures from a source of $CO_2$ and anaesthetic halocarbon at supercritical pressures. This operates for the separation of Sevoflurane or Isoflurane from Desflurane as their boiling points are significantly different (Sevoflurane 58.5° C., Isoflurane 48.5° C. vs Desflurane 23° C.).

In this method, a loop is established by the pumping of $CO_2$ to pressures of 10-40 bar into an accumulator. $CO_2$ is depressurized to 0-10 bar into a gas liquid separator. Liquid anaesthetic agent is removed into a collection vessel and gaseous $CO_2$ is recirculated to the pump to complete the loop. Into the loop is injected the purified anaesthetic halocarbons in supercritical $CO_2$. The anaesthetic halocarbons have been collected from a clinical environment onto a filter material and extracted in supercritical $CO_2$ and may but not necessarily have been purified from contaminants by supercritical chromatography. The anaesthetic halocarbons contain 2 or more of sevoflurane, isoflurane and desflurane or any other halogenated anaesthetic agent. In order to separate the Sevoflurane/Isoflurane from Desflurane, the gas-liquid separator is warmed to above the boiling point of Desflurane. Sevoflurane and Isoflurane are condensed in the gas-liquid separator but Desflurane is not condensed and cycles with $CO_2$. This process is not 100% efficient, it takes several passes through the gas-liquid separator to condense all the sevoflurane and isoflurane. Infrared detection is used to determine the anaesthetic halocarbons present in the gas flow. Once the sevoflurane/isoflurane has been condensed and removed, the temperature of the gas liquid separator is reduced to −20 to −30° C. to condense the desflurane as a separately collected fraction.

In an aspect of this invention, to separate sevoflurane/isoflurane from desflurane, the temperature of the condensing gas-liquid separator is held above the boiling point of desflurane and a closed $CO_2$ loop established to collect sevoflurane and isoflurane. After collection of this fraction is complete, the temperature of the gas liquid separator is reduced to collect the desflurane fraction.

An alternative method may be the use of fractional distillation to separate the different anaesthetic halocarbons. This is well established in the art.

In a further aspect of this invention, individual, purified anaesthetic halocarbon has been collected and all $CO_2$ removed, the product is filtered by a 40 micron and 15 micron filter and any further pharmaceutical sterilization procedure performed. It is then tested for quality and bottled for resupply.

It will be clear to those skilled in the art and from patent P34906WO that separation/condensation and chromatography could be used in any order and may be used multiple times in the same process. Furthermore, it will also be clear that the preferred fraction collection systems can be used to separate and collect any volatile halocarbon released by industry or present in the environment in addition to anaesthetic agents.

Carbon dioxide is delivered to the column system by a pump and accumulator to ensure delivery of a supercritical fluid. Thousands of litres of anaesthetic agent will need to be processed by this system. Inline IR can be used to control column injection and elution timings, but with many columns, a calibrated timing system may be preferable. Subtle differences in the resistance of each column may lead to different transit times for the anaesthetic agent. This can cause problems with collection timings when multiple columns are used.

The pump must increase the pressure of liquid $CO_2$ to supercritical pressures (above 73 bar). The liquid $CO_2$ supplied must remain liquid and therefore the pump and supplied $CO_2$ liquid is cooled to prevent liquid-gas phase change on pumping. In a preferred embodiment, the liquid $CO_2$ supply is pressurised by a pump capable of flows up to 20 litres or more per minute and supplies a pipeline pressure of preferably 80 to 110 bar, although other supercritical pressures may be used. This pipeline pressure is fed to a rack of pumps. These pumps are capable of being joined together and running from a common drive shaft, powered by an electric motor, most preferably a stepper motor. Each pump is capable of flows up to 10-500 ml/min, through a single column, although higher flows of supercritical $CO_2$ can be used with very large internal diameter chromatography columns. Each pump steps the pressure up by a small amount, preferably 2-20 bar, most preferably 5 bar. At the end of the columns, pressure is regulated in the columns by a back-pressure regulator. Each pump will produce a constant flow. Therefore, subtle resistance differences will lead to a compensatory increase in pre-column pressure that will ensure similar column retention times for the anaesthetic agents.

A pressurized common rail supplied by a high volume pump can be used to supply many individual column pumps at stable flows of 10-500 ml/minute for the purification of anaesthetic halocarbons from contaminants by supercritical fluid chromatography.

Chromatography pumps used in the purification of anaesthetic halocarbons by supercritical chromatography may share the same drive motor, most preferably a stepper motor, by the use of an interlock system that joins their cam-shafts.

This pumping system allows for consistent, cost-effective, multiple column flow regulation required for chromatography at this scale.

In a further aspect of the invention, the systems described in this application and P34906WO can be used to clean the environment of the atmosphere, either above areas of high pollution or in the upper atmosphere. Devices to achieve altitude, including but not exclusively limited to helium balloons or aeroplanes, are used to carry a halocarbon capture medium as described in P34906WO, preferably a functionalised aerogel, although silica or zeolites could be used, to the desired altitude. High flow-rate fans pass large volumes of air through the capture medium, capturing halocarbons, nitrous oxide, nitrous intermediates (NOx) as well as other environmental pollutants. The systems described in P34906WO and this application can then be used to break down nitrous oxide and nitrous intermediates using high-pressure catalytic conversion with these potentially explosive nitrogen/oxygen compounds diluted in supercritical $CO_2$ (supercritical fluids perfectly dissolve each other and nitrous oxide achieves a supercritical state at similar temperatures and pressures to $CO_2$). Halocarbons are not broken down and continue to a pressurized condenser that liquefies them or they are re-bound to a capture medium as described at atmospheric pressure. They are returned to ground level and are subjected to the processes described in P34906WO, and this invention, namely to use supercritical fluid, preferably carbon dioxide, to dissolve, purify, separate and condense halocarbons for re-sale.

This system has several important aspects. The capture medium detailed in P34906WO is an aerogel. This is the lightest solid with the largest surface area to volume ratio known. It is also fully recyclable if based on modified cellulose as described by one aspect of P34906WO. As a large surface area is required for the flow-rates required for meaningful cleaning, this is the ideal material to take into the atmosphere.

The amount of nitrous oxide intermediates in the environment far exceeds halocarbon and nitrous oxide intermediates are not economical to re-process currently. It is therefore cost-effective to catalyse the breakdown of this compound, under controlled conditions to produce nitrogen and oxygen, at the site of capture. The halocarbon can then be extracted from the aerogel using the same supercritical fluid and stored for return to the ground, perhaps leaving the airborne apparatus still in the position required for extraction rather than returning to ground.

The returned halocarbons are valuable as well as being potent greenhouse gases and ozone depleting agents. If we are able to return these compounds, separate and purify them for re-use then we can circularize the economy of their use. This will ensure the responsible use and life-cycle of an important class of chemical, namely halocarbons, that are under political pressure to be removed from use. For example, automobile air conditioning refrigerants can be purchased for a cost that includes their recapture and processing for re-use. With an efficient capture and remanufacture system, this may not be significantly more than the cost of their manufacture from raw materials. Halocarbons are inert, non-combustible and are not biologically active at environmental exposure doses. They are used in a range of industries as diverse as fire quenching systems to drug dispersion systems for inhalers. The possible circularization of this economy could have significant cost and environmental impact in the global economy.

Environmental halocarbons and NOx may be captured by placing the capture material, either silica, zeolite or a functionalised cellulosic material, most preferably an aerogel, in a container with a mesh to retain the capture material in front of fan equipment used to remove heat from air conditioning systems or car radiators. Containers will need to be fitted to the space available. These fans are in operation frequently and are concentrated in areas with high pollution, such as cities. Therefore, collection from these environments will be cost-effective. The capture material can be collected and sent for processing in which it is exposed to supercritical fluid, passed through a NOx reducing catalyst (metal oxide or precious metal) and then condensed and liquid halocarbons separated from $CO_2$ by a cooled cyclonic and inertial collection system as described in this application and P34906WO. Any condensed chemicals may be separated by supercritical fluid chromatography or fractional distillation for re-use.

The method of collecting halocarbons and pollutants such as NOx intermediates from the atmosphere onto a capture material, preferably silica, zeolite, most preferably a halocarbon functionalised cellulosic aerogel by placing the capture material in a container that fits in front of vehicle or air conditioning fan units.

The extraction of industrial halocarbons and NOx intermediates by exposure of the capture material to supercritical fluids. The breakdown of NOx intermediates by a precious metal or metal oxide catalyst when diluted in supercritical fluid and heated. The condensation and separation of valuable halocarbons. The method may comprise the step of supplying supercritical solution to a separation system for separating halocarbon from the supercritical solution. The supercritical fluid in the supercritical solution may act as a mobile phase. The separation system may comprise at least one chromatography column. The separation system may comprise a fractionating column.

The present invention also relates to methods and improvements in the synthesis of valuable anaesthetic agents such as Sevoflurane (1,1,1,3,3,3-hexafluoro-2-(fluoromethoxy)propane) and Desflurane (1,2,2,2-tetrafluoroethyl difluoromethyl ether) with improved yield and use of reactants and products by the use of supercritical carbon dioxide as a co-solvent.

Some aspect and embodiments of the present invention provide processes for the preparation of Sevoflurane and Desflurane.

Halogenated ethers are important agents for the delivery of anaesthesia via inhalation. Included among these anaesthetics are Desflurane (1,2,2,2-tetrafluoroethyl difluoromethyl ether—$CF_3CHFOCHF_2$), Isoflurane (2-chloro-2-(difluoromethoxy)-1,1,1-trifluoro-ethane—$CF_3CHClOCHF_2$) and Sevoflurane (1,1,1,3,3,3-hexafluoro-2-(fluoromethoxy)propane—$(CF_3)_2CHOCH_2F$).

Each anaesthetic agent has subtly different physiochemical properties that lead to different characteristics in their use as anaesthetic agents. Sevoflurane is sweet-smelling and therefore used for gas induction of anaesthesia. Desflurane has a low blood-gas solubility coefficient and therefore has a rapid onset and offset of action, even after periods of prolonged use. However, it is highly irritable to the airways, leading to coughing and laryngospasm. Therefore it cannot be used for gas induction of anaesthesia.

U.S. Pat. Nos. 3,683,092 (1970) and 3,689,571 (1972) specify the use of sevoflurane as an anaesthetic agent and three main mechanisms of manufacture.

Firstly, the chlorination of 1,1,1,3,3,3-hexafluoro-2-propyl methyl ether by a photo-induced reaction of 0.5-1:1 molar quantities of chlorine to hexafluoro-Z-methyl ether to form a chloromethyl ether. The chlorine is then replaced fluorine in the methyl group by adding the molar excess potassium fluoride in a mutual high boiling point solvent, sulfolane, at 120° C. or by using bromine triflouride. U.S. Pat. No. 5,886,239 (1997) states that chloromethyl 2,2,2-trifluoro-1-(trifluoromethyl)ethyl ether (chlorosevoether) can be reacted with sterically hindered tertiary amine hydrofluoride salts using chlorosevoether in molar excess rather than sulfolane as solvent. This was improved in U.S. Pat. No. 8,729,313 by the use of sevoflurane itself as the solvent instead of a molar excess of chlorosevoether.

A second process in U.S. Pat. No. 3,683,092 is the reaction of 1,3-polyfluoro-2-propanol, formaldehyde and hydrogen fluoride. Further methods based around U.S. Pat. No. 4,250,334 (1979) use the reaction of hexaflouroisopropanol (HFIP) with formaldehyde or trioxane, in the presence of hydrogen fluoride and an acid and dehydrating agent (fluorosulphonic acid/sulphuric acid or aluminium tetrafluoride). The difficulties with switching a fluorine for hydrogen are mitigated by U.S. Pat. No. 6,100,434 which claims the reaction of hexafluoroisopropanol with trioxide or paraformaldehyde in the presence of a chlorinating catalyst, alumium trichloride. This produces sevochlorane, which is then has the chlorine substituted for fluorine by reaction with potassium fluoride in the presence of a potassium base (Potassium carbonate) dissolved in a solvent such as polyethylene glycol (PEG) at a temperature of 85-95 degrees Centigrade. Water is added as a lewis base to reduce the breakdown of sevochlorane by the reaction product alumium hydroxydichloride, which ultimately needs to be removed from the process and recycled back to aluminium trichloride.

Aspects of the invention relate to the use of supercritical carbon dioxide as a solvent in both processes described above. Carbon dioxide ($CO_2$) has a critical pressure of 7.29 MPa and critical temperature of 31.1 degrees centigrade. When above critical pressure and temperature, it exists as a supercritical fluid. Supercritical fluids have no surface tension and the properties of both a liquid and a gas. They expand to fill the container they are in but also have a density-dependent ability to dissolve substances like a liquid. Supercritical $CO_2$ is a non-polar solvent, but may be able to dissolve some polar compounds by the use of a modifier such as methanol. Halocarbons including the fluoroether anaesthetic agents such as Desflurane, Sevoflurane and Isoflurane are highly soluble in supercritical $CO_2$ as they are non-polar. The concentration of reactants can be varied in proportion to $CO_2$. Furthermore, temperatures and pressures above the critical temperature and pressure of carbon dioxide can be used with dilution to control reaction rate. Therefore, supercritical $CO_2$ is an ideal reaction solvent for the formation of the above mentioned fluoroethers.

One further advantage to the use of supercritical carbon dioxide is that it can readily be used as a mobile phase in supercritical fluid chromatography. Supercritical chromatography is able to separate out reactants and products by their different retention-times in columns based on polarity (dipole or hydrogen-bonding), diffusivity or size-exclusion. Detection systems based on ultraviolet (UV), Infra-red (IR) absorbance spectra, mass spectrometry (MS), photoacoustic spectroscopy (PAS) or acoustic resonance spectroscopy (ARS) can be used to detect individual compounds as they leave the column and separate them by influencing the position of valves by a computerised controller. In this invention, these methods can be used to remove unwanted products and return desired reactants to the reaction vessel. If further reactants are added as required, a continuous reaction can be developed, in which the desired product is removed and collected, useful reactants are returned to the reaction vessel in the correct quantities, and unwanted products are removed for further processing.

The final advantage of supercritical $CO_2$ is its use as a gaseous mobile phase during depressurisation below critical pressure to drive fractionation of volatile compounds by their volatility. The supercritical mixture of carbon dioxide and volatile compound is depressurised (to any subcritical pressure) and heated to prevent freezing at the back pressure regulator, vaporising both the carbon dioxide and any volatile product. This product can then be passed to an expansion vessel and fractionating column set at subcritical pressure and the desired temperature to condense a single volatile fraction but leave more volatile fractions in gaseous form to be selected in further columns or returned to the expansion vessel for multiple cycles to ensure fraction separation.

In this invention, sevoflurane ($(CF_3)_2CHOCH_2F$) can, for example, occur via two methods, both using supercritical $CO_2$ as the solvent.

In an embodiment, chlorosevoether (chloromethyl 2,2,2-trifluoro-1-(trifluoromethyl)ethyl ether dissolved in supercritical $CO_2$ is reacted with a sterically-hindered tertiary amine hydrofluoride salt at temperatures above the critical temperature of $CO_2$ (31.1 degrees C.) and pressures above the critical pressure of $CO_2$ (7.29 MPa) in a reaction chamber fed by a pump supplying $CO_2$ from a cylinder and a pump supplying chlorosevoether. A flow of supercritical $CO_2$ and reactants from the pumps maintains the pressure in the chamber as the supercritical mixture is withdrawn from the chamber to be passed through chromatography columns, fractional separation unit or both systems combined. Chromatography and/or fractional separation are used to remove unwanted products, collect the desired product and return useful reactants to the reaction chamber via the reactant pump. The concentration of reactants and products is continuously measured by the use of UV, IR, MS or PAS or ARS, influencing the flow of supercritical $CO_2$ and reactants and the temperatures and pressures of the reaction.

This invention has the advantage of using an environmentally friendly solvent that is able to control the reaction rate by varying dilution, temperature and pressure as the reaction proceeds. Furthermore, by combination with chromatography and fractional separation systems, wanted products and reactants can be selectively captured or re-used and unwanted products removed. Finally, the flow of the supercritical solution through the process allows sampling of the concentrations of the reactants and products so that the optimal reaction conditions can be maintained and further reactants added as required.

In a further embodiment, a mixture of hexaflouroisopropanol (HFIP) with equimolar or excess molar concentrations of paraldehyde or trioxane are dissolved in supercritical $CO_2$ in a chamber fed by a $CO_2$ cylinder, $CO_2$ pump and reactant pump. These reactants are then passed under the flow of supercritical solution to a chamber containing aluminium trichloride. As the reactants flow through the second chamber, they form sevochlorane. The flow of supercritical solution is determined to ensure adequate conversion to sevochlorane, but minimal breakdown of the sevochlorane by aluminium hydroxydichloride. The supercritical mixture passes to a second reaction chamber in which potassium fluoride is added with or without water to replace the chlorine with a fluorine, forming sevoflurane. The temperature of the second reaction chamber may be different from the first chamber, but must be above the critical temperature of carbon dioxide. The supercritical mixture passes into a multi-column chromatography system, fractional separation system or both to allow the separation of different reactants or products. Sevoflurane can be purified and collected and reactants recycled to their respective reaction chambers. Purified carbon dioxide can be re-pressurised and re-used.

This second embodiment uses supercritical $CO_2$ as a preferred solvent to sevochlorane or sevoflurane. This enables a faster reaction time and reduced breakdown of sevochlorane and sevoflurane by the alumium hydroxydichloride. Furthermore, the sevochlorane exposure-time to the alumium trichloride/aluminium hydroxydichloride can be controlled. The aluminium hydroxydichloride chamber can then be re-activated by converting aluminium hydroxydichloride to aluminium trichloride when outside of the preferred system. Supercritical $CO_2$ is an ideal solvent for the fluorination of the sevochlorane by potassium fluoride, preventing product breakdown. Finally, supercritical chromatography and/or fractionation driven by $CO_2$ depressurisation can be used to recycle useful reactants, purify the product and remove unwanted products under monitoring by UV, IR, MS, PAS or ARS.

Desflurane (1,2,2,2-tetrafluoroethyl difluoromethyl ether—$CF_3CHFOCHF_2$) is synthesised by the fluoro-substitution of isoflurane (2-chloro-2-(difluoromethoxy)-1,1,1-trifluoro-ethane). This can be carried out by elemental fluorine in a fluorinated solvent (Freon E3) or in fluorine gas in argon at cryogenic temperatures as in U.S. Pat. No. 3,897,502, however the use of elemental fluorine is hazardous. U.S. Pat. No. 6,054,62 uses transition metal fluorides, preferably cobalt but suffers from poor yield and by-product formation. U.S. Pat. No. 6,800,786 shows the reaction of isoflurane with optimum quantities of hydrogen fluoride in the presence of an antimony pentachloride catalyst. US Patent number 20060205983 A1 states the use of antimony pentafluoride to reduce the molar excess of hydrogen fluoride. Both antimony pentafluoride and pentachloride are expensive catalysts that are discarded after use.

EP 341,005B details the reaction of isoflurane with sodium or potassium fluoride at high temperatures (278 degrees C.) and pressures of 500 psi in the absence of a solvent over a long period of time. This is a batch process and requires a long reaction time. GB 2,219,292A specifies the reaction of isoflurane with an alkali metal fluoride in sulpholane in the presence of a phase transfer catalyst at 210 degrees C.

In the third embodiment of this invention, isoflurane is supplied to a thermally controlled reaction vessel containing solid potassium fluoride, supplied by a high-pressure pump, with $CO_2$ supplied with the isoflurane via a separate high pressure pump. The isoflurane is dissolved and diluted in supercritical $CO_2$, although the concentration of isoflurane is high 50-99%. The pressure of the chamber is increased to 80-200 bar, most preferably 80 bar, and the temperature to 31 to 300 degrees Celsius, most preferably 200-275 degrees Celsius. The mixture remains in the reaction chamber for 1 to 15 hours, most preferably 5-10 hours before the reaction chamber is flushed with supercritical $CO_2$ to remove and dilute reactants and products. Products and reactants are condensed by gas-liquid separator and separated by chromatography or fractional separation using $CO_2$ or conventional fractional distillation as described. This synthetic reaction can be arranged with a continuous flow of reactant/$CO_2$, delivered at a flow rate that ensures an appropriate transit time to ensure complete conversion of isoflurane to desflurane.

Potassium fluoride, sodium fluoride or anhydrous fluorine are added to the mixture at concentrations that control the exothermic nature of the reaction. Alternatively gaseous fluorine can be added to the carbon dioxide. When compressed above the supercritical pressure of $CO_2$, fluorine itself is in a supercritical state. As supercritical fluids dissolve each other perfectly, this would be an ideal reaction mixture. If the reaction rate is too slow at or just above the critical temperature of $CO_2$ (31.1 degrees C.), the reaction mixture can be passed through a reaction chamber containing antimony pentahalide, a transition metal trifluoride (for example cobalt trifluoride), transition metal oxide (such as chromia) or mixed with a phase transfer catalyst such as tetramethylammonium chloride to reduce the temperature required for the reaction to proceed without requiring high temperatures that may cause an increase in the cleavage of the carbon-oxygen bond leading to fragmentation products. This flow is driven by the continued input of supercritical $CO_2$ and reactants at the start of the process.

The mixture is then delivered to a supercritical chromatography and/or fractionation system which separates out the product, recycles useful reactants and wastes unwanted products.

Advantageously, this third embodiment allows the controlled dilution of the reactants at pressures and temperatures that allow the reaction to proceed. Thus rates of conversion and the exothermic nature of the reaction can be controlled. This is a continuous system that does not waste catalysts and allows a high through-put and reduced costs compared to prior art. Finally, due to the use of chromatography and/or fractionation, recycling of useful reactants and the collection of a purified product can occur. This can all be under the control of feedback from UV, IR, MS, PAS or ARS.

The present invention also provides a method of manufacturing sevoflurane and/or desflurane including the use of supercritical carbon dioxide as a solvent.

The present invention also provides a method of manufacturing 1,1,1,3,3,3-hexafluoro-2-(fluoromethoxy)propane including the use of supercritical carbon dioxide as a solvent.

The present invention also provides a method of manufacturing 1,2,2,2-tetrafluoroethyl difluoromethyl ether including the use of supercritical carbon dioxide as a solvent.

Different aspects and embodiments of the invention may be used separately or together.

Further particular and preferred aspects of the present invention are set out in the accompanying independent and dependent claims. Features of the dependent claims may be combined with the features of the independent claims as appropriate, and in combination other than those explicitly set out in the claims.

BRIEF DESCRIPTION OF DRAWINGS

Embodiments of the present invention will now be described, by way of example only, with reference to the accompanying drawings, in which like components are assigned like numerals, and in which:—

Figure 1:
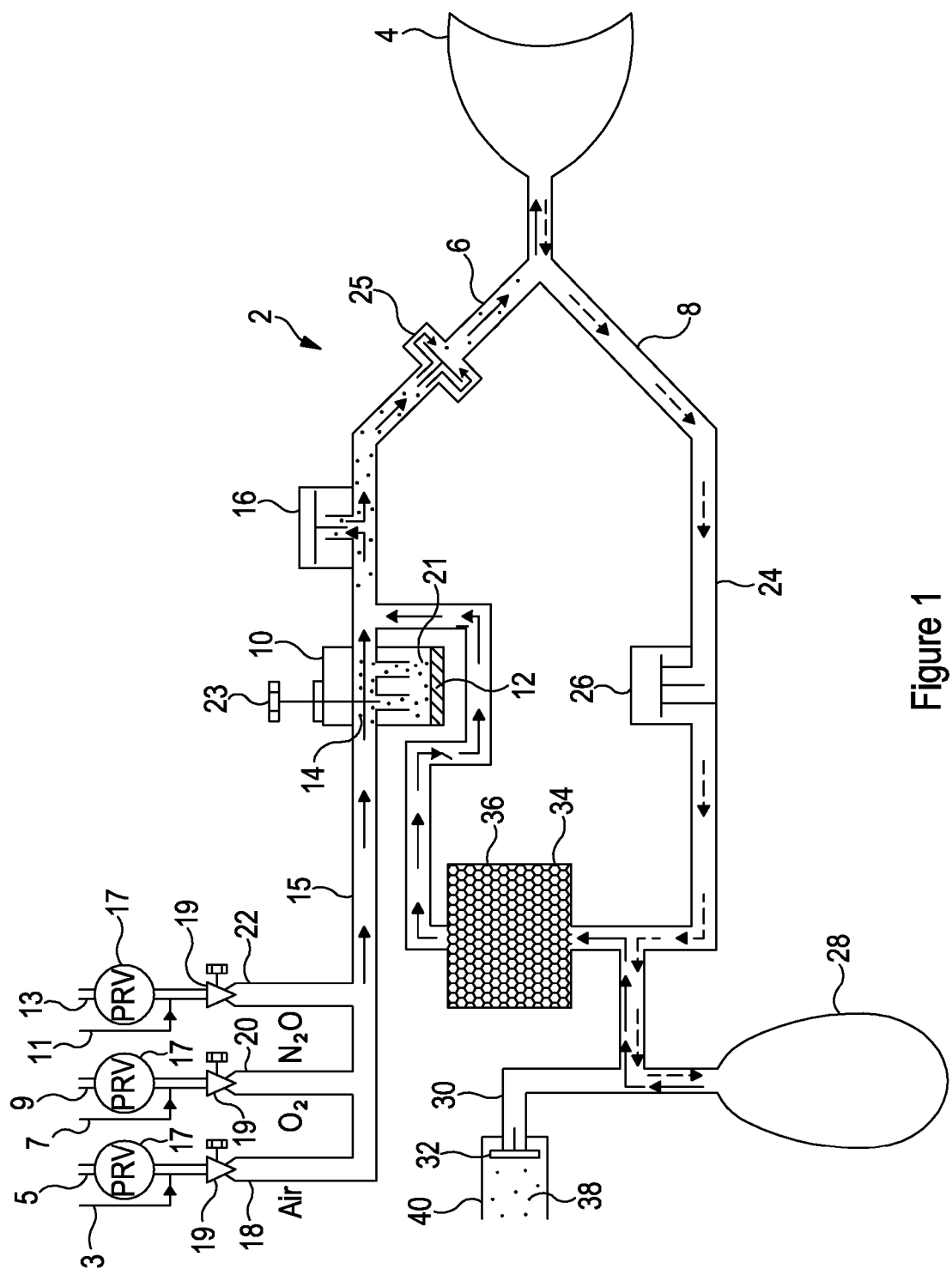
FIG. 1 is a schematic diagram of an anaesthetic machine and breathing circuit according to P34906WO

The example embodiments are described in sufficient detail to enable those of ordinary skill in the art to embody and implement the systems and processes herein described. It is important to understand that embodiments can be provided in many alternate forms and should not be construed as limited to the examples set forth herein.

Accordingly, while embodiment can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

Unless otherwise defined, all terms (including technical and scientific terms) used herein are to be interpreted as is customary in the art. It will be further understood that terms in common usage should also be interpreted as is customary in the relevant art and not in an idealized or overly formal sense unless expressly so defined herein.

All orientational terms are used in relation to the drawings and should not be interpreted as limiting on the invention.

DETAILED DESCRIPTION

Figure 2:
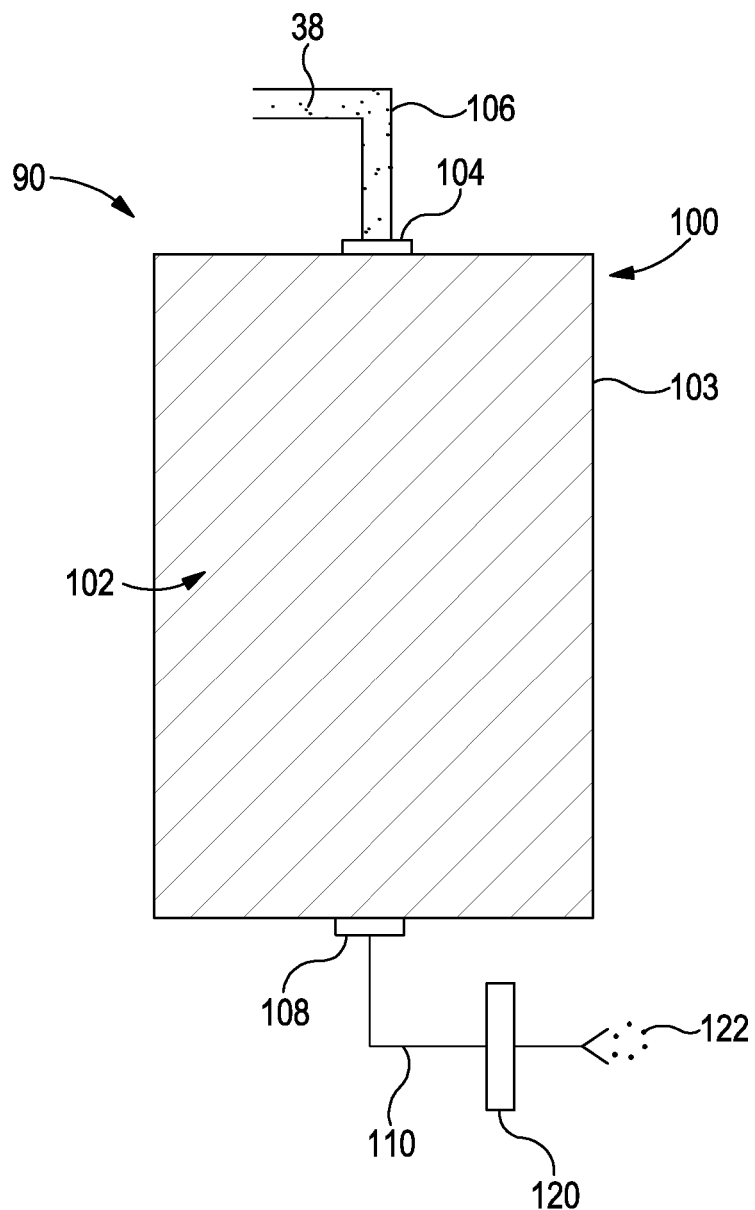
FIG. 2 is a schematic diagram of a pressure tolerant capture canister containing a filter material for the capture of anaesthetic halocarbons from the exhaust of a single or many anaesthetic machines as detailed in P34906WO.

FIG. 2 shows a system 90 for the capture of anaesthetic halocarbons as detailed in P34906WO.

Exhaust gases from the anaesthetic machine 38 are passed via a conduit 106 through a connector 104 into a canister 100 made of material 103 that is tolerant of supercritical pressures. This canister 100 contains the filter material 102 that captures the anaesthetic agent from the exhaust gases 38. Scrubbed gas then exits the canister via an exit conduit 108 and pipe 110 to pass through a charcoal filter 120 before being exhausted to the atmosphere 122.

Figure 3:
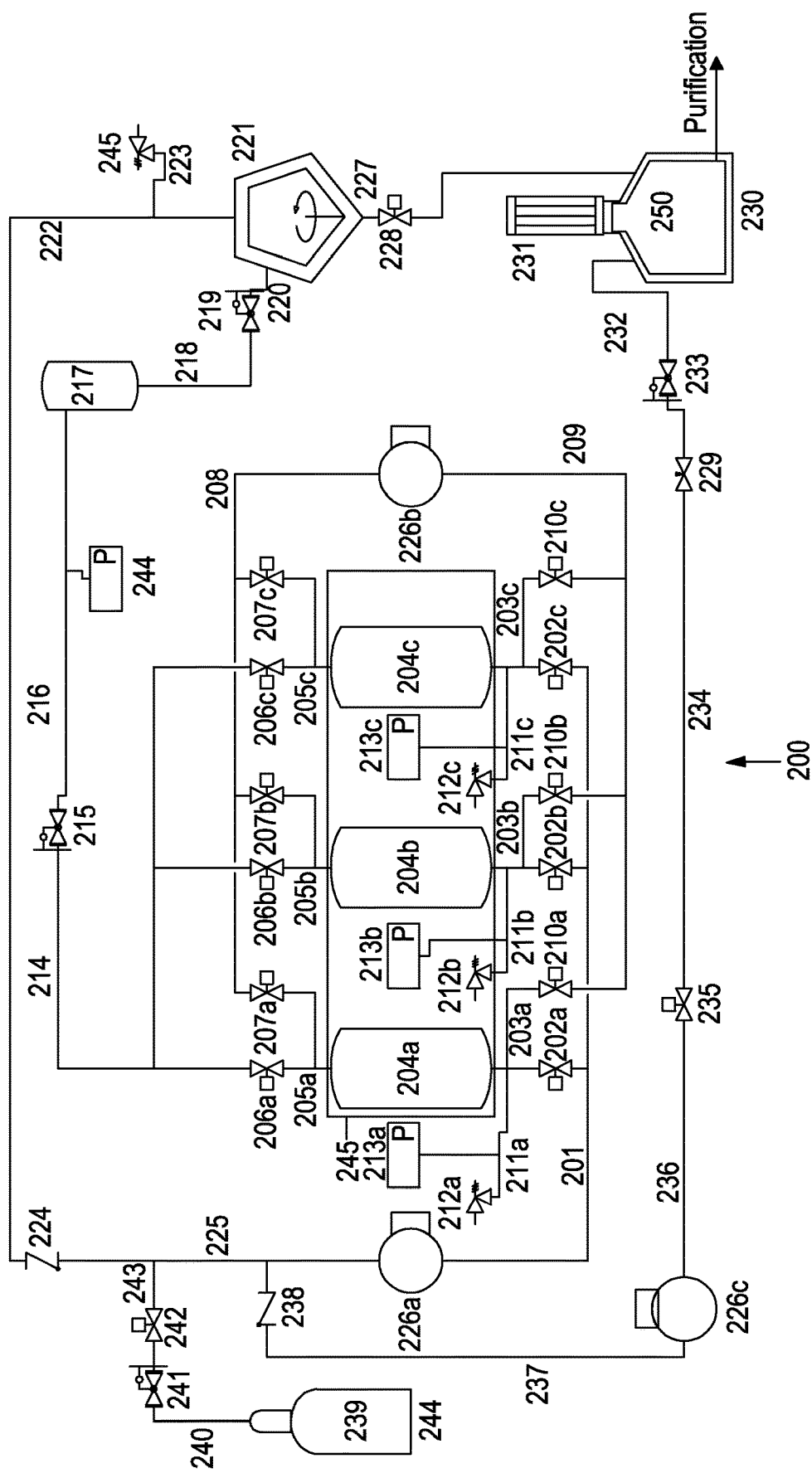
FIG. 3 is a schematic diagram of a system for the extraction and condensation of anaesthetic halocarbon from a capture vessel (be it sleeve contained in a pressure vessel or pressure-tolerant canister) using supercritical fluids, with conservation of gas within the system.

A system 200 to extract and condense anaesthetic halocarbons captured onto a filter material using supercritical fluids is shown in FIG. 3.

Figure 5A:
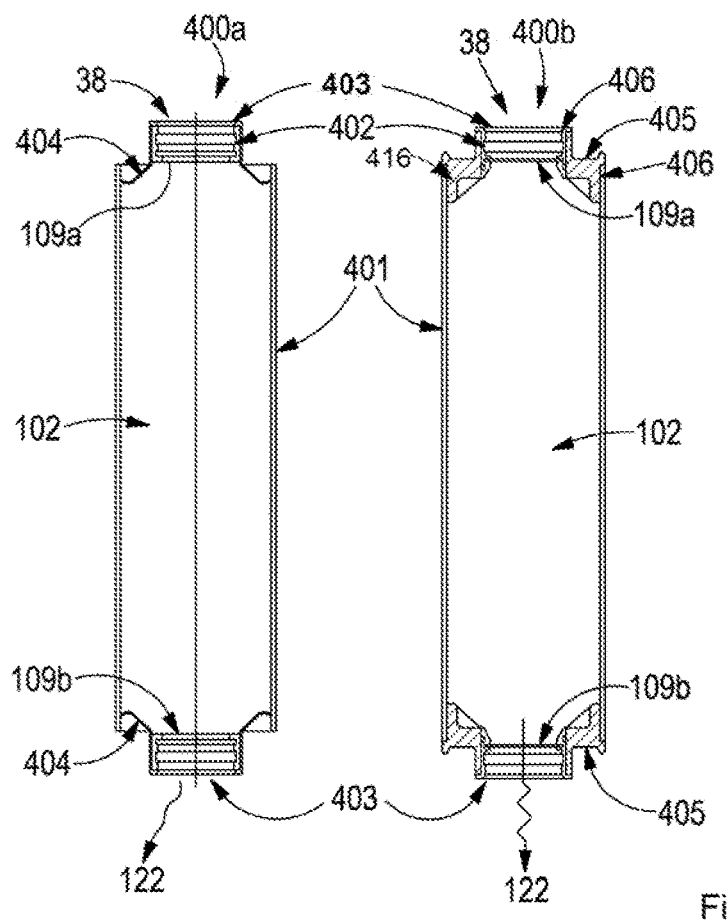
FIGS. 5A-5B show a schematic diagram of a pressure vessel with two different designs of pressure-intolerant sleeve for the capture and extraction of anaesthetic halocarbons from a filter material.
Figure 5B:
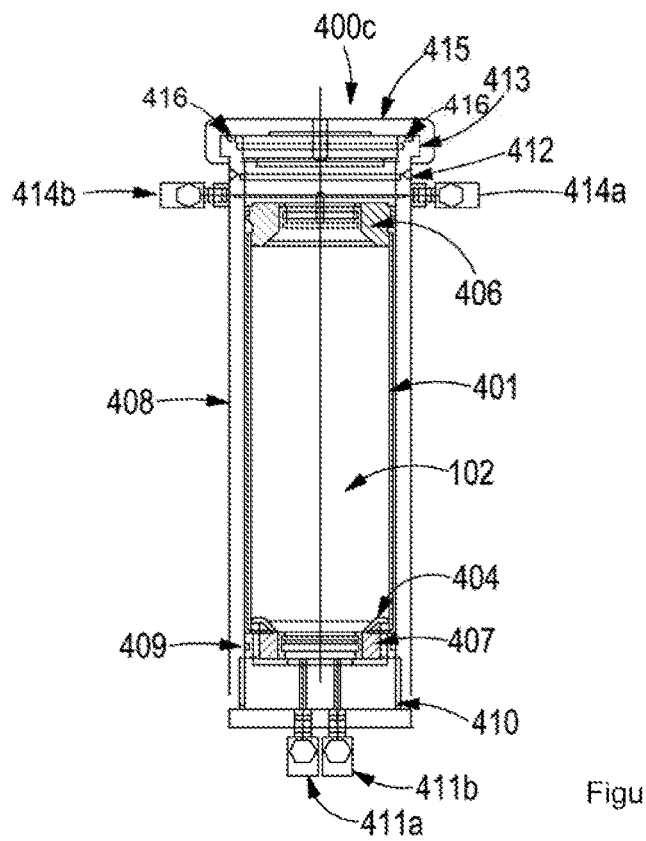
Figure 6:
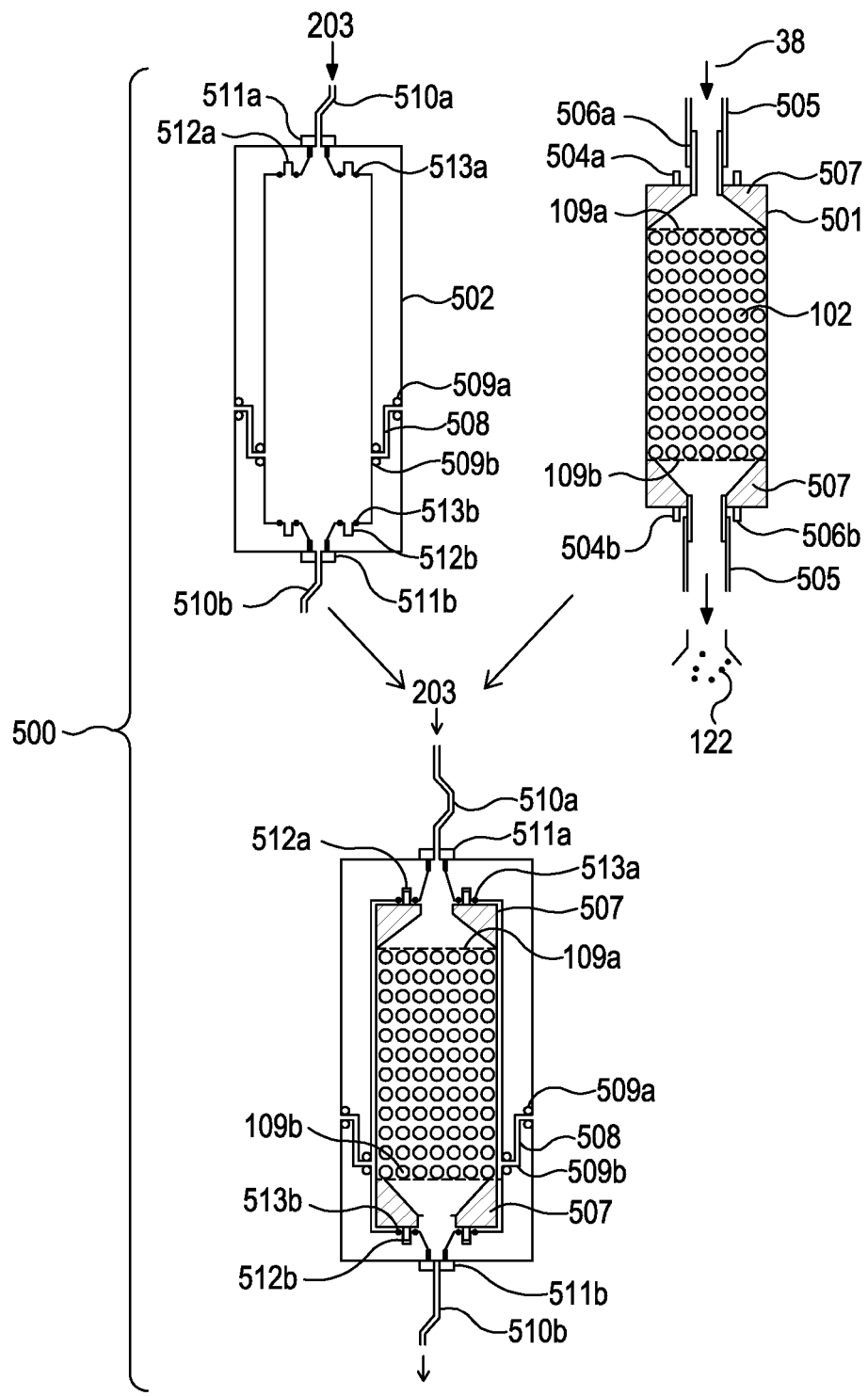
FIG. 6 is a schematic diagram of a pressure-intolerant sleeve that can be used to capture anaesthetic agent onto a filter material as described in patent P34906WO and in this application. This sleeve is then inserted into a pressure-tolerant chamber for subsequent supercritical fluid extraction of anaesthetic agent from the filter material.

Anaesthetic halocarbons are captured onto a filter material 102 as detailed in FIG. 2 or FIGS. 5A-5B and 6. In FIG. 2, the canister is pressure-tolerant and therefore can be connected to a supply of supercritical fluid directly. In FIGS. 5A-5B and 6, the filter material 102 is contained within a pressure-intolerant sleeve and must be contained within a pressure vessel to extract anaesthetic halocarbons. For the purposes of FIG. 3, the vessels 204a, 204b and 204c are either:

1. A pressure tolerant canister 100 containing anaesthetic halocarbons captured onto a filter material 102.

2. A pressure intolerant sleeve 501 or 401 containing anaesthetic halocarbons captured onto a filter material 102 inside a pressure tolerant chamber 502 or 402.

Carbon dioxide gas 239 is supplied from a cylinder 244 at a pressure of 50 bar via a pressure reducing valve 241 to a pressure of 20 bar and solenoid valve 242 under the control of a pressure switch 244. $CO_2$ passes through the input line 243 to the common line 225 and to the compressor 226a. This increases the pressure and temperature of the $CO_2$ up to supercritical pressure of 80 bar and temperature of 40 degrees C. Supercritical $CO_2$ flows through the vessel input line 201 through solenoid valves 202a, b, c through the pressure vessels 204a, b, c containing filter material (not shown) with captured anaesthetic halocarbon. The pressure vessels are contained in a heated chamber 245 at 31-60 degrees Celsius although higher temperatures may be used.

The supercritical solution of $CO_2$, anaesthetic halocarbons and any contaminants captured from the anaesthetic exhaust and extracted by supercritical $CO_2$ passes through output lines 205a, b, c to solenoid valves 206a, b, c and into a common output line 214 to a back pressure regulator 215, set to maintain the pressure vessels at 80 bar. The solution (now at less than supercritical pressure and temperature) passes through the line 216 to an accumulator 217 where a buffer stores pressurized supercritical solution at 40-50 bar under the control of the pressure switch 244 and the $CO_2$ input solenoid valve 242. If the pressure in the accumulator drops to less than 40 bar, more $CO_2$ is added to the system by the valve 242 and the pressure increases to 50 bar when the pressure switch 244 closes the input valve 242.

The solution passes through a transfer line 218 to a pressure reducing valve 219 to a pressure of 10 bar with a very short transfer line 220 or incorporated into a gas-liquid separator 221. This separator is cooled by a thermal jacket to −20 degrees C. (for Sevoflurane/Isoflurane, lower temperatures may be used for Desflurane). Upon depressurization of $CO_2$ and adiabatic expansion, the temperature in the gas-liquid separator may drop to −30 to −40 degrees Celsius at certain points. The $CO_2$ remains just above the temperature at which it would condense. The anaesthetic halocarbon condenses and its vapour pressure drops to at or near zero. It is collected by centrifugal and inertial impact into the bottom of the gas-liquid separator. Gaseous $CO_2$ leaves the gas liquid separator 221 by an exhaust line at the top of the separator 222. A pressure relief valve 245 connected to the exhaust 223 prevents over-pressure of the separator. The $CO_2$ returns to the compressor 226a by a one way valve 224 and common input line 225 and is returned to the extraction chamber 204a, b, c as described. Therefore, once pressurized, a continuous circle is formed in which the $CO_2$ is repressurised and recirculated to deliver further extraction. The pressures of the chambers are detected by pressure gauges 213a, b, c and prevented from overpressure by pressure relief valves 212a, b, c via transfer lines 211a, b, c, although these systems may be common.

Condensed liquid anaesthetic at 10 bar and −20 degrees Celsius at the bottom of the gas liquid separator 221 passes through a transfer line 227 and solenoid valve 228 to a temperature controlled tank 230 becoming stored anaesthetic 250. Initially the tank is at −20 degrees Celsius. A level indicator (not shown) in the tank 230 switches off the solenoid valve 228 to isolate the tank and the tank is depressurised through a pressure reducing valve 233 and flow restrictor 229, feeding $CO_2$ (and a small amount of anaesthetic agent) back through a transfer line 234 and solenoid valve 235 to a compressor 226c that increases the pressure up from atmospheric pressure to 10 bar, where is passes through a one way valve 238 into the common input line 225. Once the pressure is reduced to atmospheric pressure, the solenoid valve 235 is closed and the tank is warmed up to room temperature gradually with the tank now opened to a reflux condenser 231 that prevents the escape of any anaesthetic halocarbon but allows any remaining $CO_2$ dissolved in the anaesthetic agent at negative temperatures to escape (not shown). The reflux condenser is maintained at −30 degrees Celsius.

The system 200 operates in groups of 3 pressure vessels. As an example, one vessel, 204a has finished extraction and 204b and c are full of anaesthetic halocarbon. The flow of $CO_2$ is stopped into 204a by the solenoid valves 202a and 206a and passes through 204b under the opening of solenoid valves 202b and 206b. The contents of 204a are still pressurized and some anaesthetic halocarbon may remain. The contents of 204c are unpressurised. Therefore, solenoid valves 207a and 210c open and the contents of 204a are transferred down a pressure gradient and then pumped into 204c by the action of the compressor 226b. Vessel 204a is emptied down to a slight vacuum, a relief valve opens (not shown, in similar position to pressure relief valve 212a), and the vessel is equilibrated with the environment. The canister or sleeve can now be changed for another sleeve or canister which is full of anaesthetic halocarbon. Pressure vessel 204c is now pressurized and when 204b has finished being extracted, flow of $CO_2$ is switched to 204c and a transfer of the remaining contents of 204b to 204a occurs as described above.

By this cycle, the pressurized contents ($CO_2$ and remaining anaesthetic halocarbon) are not lost when each sleeve or canister is changed. It is expected that the opening and exchange of sleeves/canisters will be by an automated pick and place system familiar to those skilled in the art of industrial automation.

Figure 4:
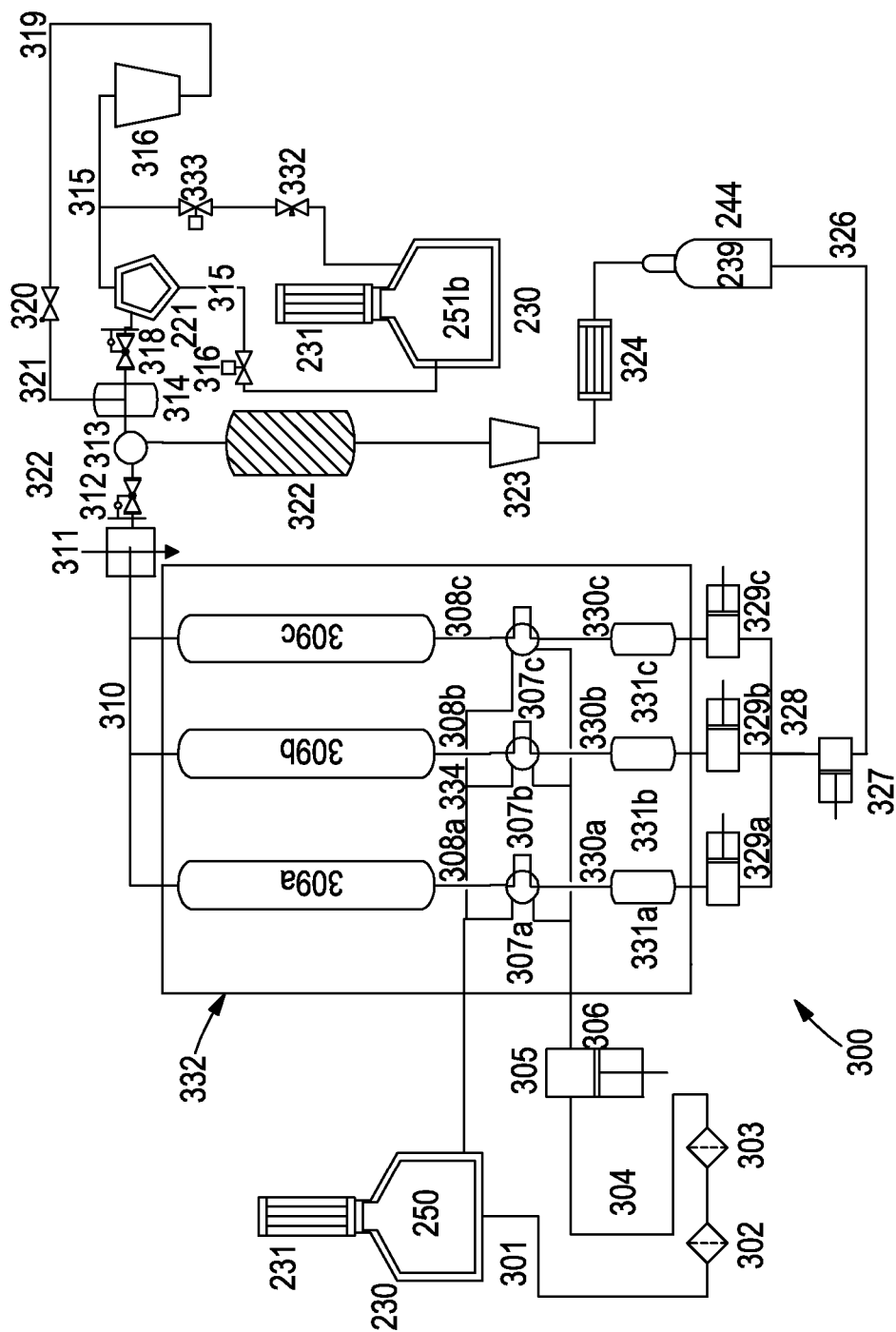
FIG. 4 is a schematic diagram of a system of purification and condensation of anaesthetic halocarbon by supercritical fluids, with conservation of gas within the system.

FIG. 4 shows a chromatography system 300 that purifies and condenses anaesthetic halocarbon. This system can be used as primary removal of non-halocarbon contaminants or secondary removal of halocarbon contaminants with or without the separation of the individual anaesthetic halocarbons. A modifier may be added to improve separation (not shown).

Carbon dioxide 239 contained in a cylinder 244 at around 50 bar is transferred by liquid draw 326 to a pump 327 that increases the pressure to 75 bar to supply a backbar 328. Pumps 329a, b, c with non-return valves (not shown) increase the pressure further to 80 to 100 bar and each separately supply an accumulator 331a, b, c respectively and supply line 330a, b, c inside a warmed compartment to 40 degrees Celsius 332. These supply lines each feed a rotary valve 307a, b, c. Extracted liquid anaesthetic halocarbon 250, including certain contaminants, either produced and exhaled by the patient or as anaesthetic agent breakdown products, is supplied from the tank 230 through 40 micron and 15 micron filters 302, 303 and a transfer line to a pump 305. The pump supplies a common input line to each rotary valve 307a, b, c that loads a fixed volume loop of 2-50 mL internal volume. Liquid 250 is returned to the tank in a continuous motion through an outlet in the rotary valve. To load the contents of the loop into the column, the rotary valve 307a, b, c is turned under stepper motor control to the 'load' position to link the loop to the $CO_2$ input 330a, b, c and the chromography columns 309a, b, c via short transfer lines 308a, b, c. This disengages the loop from the flow to and from the tank 230 and the pump 305 stops. After enough $CO_2$ has passed through the loop to flush the liquid anaesthetic halocarbons 250 onto the columns 309a, b, c, the rotary valves 307*a, b, c* rotate back to the 'fill' position. $CO_2$ passes through the column without going through the loop to continue chromatography and the loop discharges the $CO_2$ contained within it to the tank 230, where it is vented through the reflux condenser 231 without the loss of anaesthetic halocarbons, and is refilled with filtered liquid anaesthetic 250 by the pump 305.

Chromatography proceeds through the columns 309*a, b, c*. The anaesthetic agent is separated from contaminants (depending on which column is being used). The anaesthetic agents exit the column first into transfer pipe 310, are detected by Infra-red detection 311 and a rotary valve 313 discharges the anaesthetic fraction after passing through the back pressure regulator 312 into a condensation circuit. The condensation circuit starts with a small accumulator 314 leading to a pressure reducing valve 318 to take the pressure down to 10 bar. This leads to a thermally controlled gas liquid separator 221 at −20 to −30 degrees Celsius. Gaseous $CO_2$ exits the gas liquid separator 221 via transfer pipe 315 to a compressor 316 that increases the pressure to 55 bar and warms the gas to 35 degrees Celsius. The gas then passes through transfer line 319 to through a one way valve 320 and line 321 to the accumulator, completing a loop. This loop may be charged by an input of $CO_2$ from a tank (not shown), however, once charged, requires no further $CO_2$. This loop runs continuously, and is added to by injections of anaesthetic halocarbon and $CO_2$ from the columns as determined by the Infrared sensor 311. Purified liquid anaesthetic halocarbon 251*b* passes through the transfer line 315 and solenoid valve 316 to a thermally controlled collection tank 230 and when full is depressurised via a flow restrictor 332 and solenoid valve to the compressor 316 to ensure anaesthetic agent is not lost. Once depressurised, the anaesthetic agent may be warmed to remove any remaining $CO_2$ (depending on the stage in the process) and anaesthetic halocarbon retained by reflux condenser 231.

Non-anaesthetic waste is diverted by the rotary valve 313 to a capture canister filled with silica and then activated carbon 322 to remove contaminants. This $CO_2$ is then filtered (not shown), compressed 323 and condensed 324 to return to the cylinder 244 as liquid $CO_2$ 239.

FIGS. 5A-5B show two different designs of pressure-intolerant sleeve 400*a* and 400*b* and a pressure-tolerant vessel 400*c* into which the sleeve locates for extraction.

Both sleeves 400*a* and 400*b* are made of a stainless steel tube 401. In 400*b*, this tube is tolerant of supercritical pressures with a minimal factor of safety. In 400*a*, this tube can be completely intolerant of supercritical pressures. In 400*a*, the ends are closed by a stainless steel cap 404, containing an egress/ingress port 403. This port is the same at either end but could be different for direction-specific loading. The cap is welded to the stainless tube 401. In 400*b*, the cap 405 is a plastic insert with a connected stainless steel insert 406 to form the ingress/egress port. This plastic cap 405 is set on seals 406 to connect it to the tube 401. The caps at either end are the same, but could be different if uni-directional loading was required.

During collection, waste gas 38, enters the sleeve via ingress port 403 which is connected to the waste anaesthetic source by a connector (not shown). The ingress port has an internal lip 402 to facilitate mechanical pick up and automation. The ingress port ends with a mesh 109*a* containing the filter material 102. This filter material captures the waste anaesthetic halocarbon. Uncaptured gas exits the canister through the mesh 109*b* and egress port and may be captured onto a charcoal canister (not shown) or enter the scavenging system (not shown) or be directly exhausted as a gas into the atmosphere 122.

Once loaded with captured anaesthetic halocarbon, the sleeve is loaded into the pressure vessel 400*c*. The pressure vessel is a stainless steel tube 408 tolerant of supercritical pressures above 73 bar (preferably 100-400 bar although higher pressure tolerance could be used). This tube is sealed 409 and screws into a base 410 with a moulded insert 407 that houses the cap of the sleeve 400*a* or 400*b*. When using sleeve 400*a*, a small channel is provided through the moulding 407 to allow the outside of the sleeve to pressurize (not shown). The other end of the tube 408 is sealed 412 with a lid 415 that fits by bayonet fitting 413 onto the tube 408. A moulding 406 in the lid houses the cap of the sleeve 400*a* or 400*b* with channels 416 to allow the passage of $CO_2$. The base 410 and lid 415 have channels 416 through the stainless steel and mouldings to allow the passage of $CO_2$. Two inlet 411*a* and 411*b* and two outlet 414*a* and 414*b* are provided although fewer or more can be used. Flow can be either from 411(*a* or *b*) to 414(*a* or *b*) or from 414(*a* or *b*) to 411(*a* or *b*).

In the case of sleeve 400*b*, when pressurized, the cap 405 moves on the seal 406 upwards and compresses itself into the pressure vessel mouldings 406, 407. These mouldings have a seal at either end (not shown) to seal the sleeve into the moulding. Therefore, flow only goes through the sleeve and not around the sleeve as it does with 400*a*. The cap is retained by the mouldings and the tube 401 is pressure-tolerant and maintained within the pressure vessel for safety. This system prevents exposure of the outside of the sleeve to supercritical $CO_2$ and possible incorporation of chemicals on the external sleeve surface into the flow of anaesthetic halocarbon. However, it allows the use of a sleeve that would not be able to withstand pressure on its own and can therefore be made of thinner, cheaper, bulk produced materials that ensure that the sleeves are cost-effective.

A system 500 to capture and elute anaesthetic agent from the anaesthetic machine and theatre environment 38 is shown in FIG. 6.

Anaesthetic agent and waste gases 38 enter a pressure-intolerant sleeve 501 from standard scavenging piping 505 coupled to an ingress conduit 506*a*. The ingress conduit 506*a* screws into threading incorporated into the sleeve 501. Anaesthetic gas flow is dispersed into the container by baffles 507 made of plastic or metal that does not absorb/react with anaesthetic gases or supercritical fluids. The waste gases 38 then pass through an intake mesh 109*a* into the filter material 102, which captures the anaesthetic agent from the waste gas flow 38. Waste gases depleted of anaesthetic agent then pass through the exit mesh 109*b* and are directed to the egress conduit 506*b* by baffles 507. Waste gases then pass from the egress conduit 506*b* into standard scavenging piping 505 for subsequent extraction to the environment 122.

Extraction requires pressures above the critical pressure of carbon dioxide 72.9 bar, therefore a chamber made of a suitable material, preferably stainless steel, and designed to tolerate these pressures is required. This chamber 502 is divided into two portions that are reversibly connected, preferably by a machined thread 508 and sealing washers 509*a* and 509*b*, so that the pressure-intolerant sleeve 501 could be inserted into the pressure-tolerant chamber 502 and the chamber sealed for supercritical fluid extraction. Super-critical fluid 203, preferably carbon dioxide, enters the chamber through a standard $\frac{1}{8}^{th}$ inch ingress piping 510*a* through intake conduit 511*a*. The chamber has a recess 512*a* and 512*b* with sealing washers 513*a* and 513*b*. The recesses 512*a* and 512*b* tightly fit the intake sealing rings 504*a* and 504*b* respectively on the pressure-intolerant sleeve 501 when in the chamber and prevent supercritical fluid from bypassing the sleeve 501 and the filter material 102.

For extraction, both portions of the pressure-tolerant chamber 502 are placed around the pressure-intolerant sleeve 501 with the intake sealing rings 504*a* and 504*b* located within their recesses 512*a* and 512*b*. As the chamber is closed, pressure is generated that seals the pressure-intolerant canister against sealing washers 513*a* and 513*b* to prevent supercritical fluid 203 from bypassing the filter material 102 contained in the sleeve 501. Supercritical fluid 203 is passed into the chamber 502 and sleeve 501 through ingress standard piping 510*a* and ingress conduit 511*a*. Supercritical fluid 203 traverses the intake mesh 109*a* and passes through the filter material 102, dissolving anesthetic agent captured from the waste gases 38. This supercritical solution passes through the exit mesh 109*b* to the egress conduit 511*b* and egress piping 510*b* for subsequent purification by chromatography or fractional separation as described in patent application P34906WO.

Figure 7:
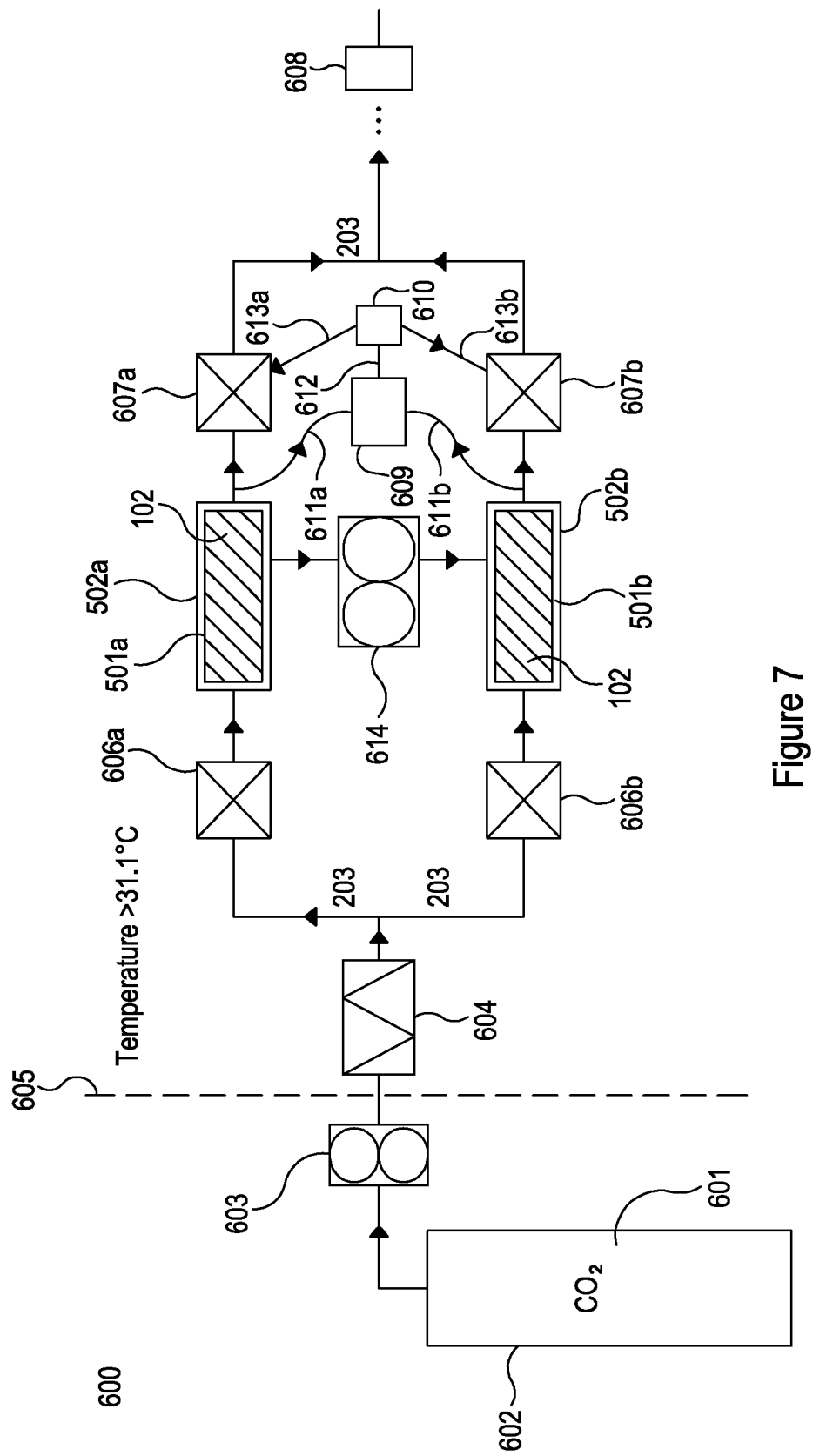
FIG. 7 is a schematic diagram of a system for transferring remaining anaesthetic agent dissolved in supercritical fluid from one canister at the end of elution to the next canister.

A system for the loading and unloading of supercritical fluid 600, preferably carbon dioxide, into sequential chambers to conserve carbon dioxide, anaesthetic agent and energy is shown in FIG. 7.

Carbon dioxide 601 contained in a cylinder 602 is pumped 603 into an accumulator 604 in a temperature controlled environment 605, above the critical temperature of carbon dioxide 31.1 degrees centigrade. Carbon dioxide 203 flows into a limb of the elution circuit via open valve 606*a* while valve 606*b* is closed. Carbon dioxide passes into a pressure-tolerant chamber 502*a* containing a pressure-intolerant sleeve 501*a* filled with filter material 102 that has absorbed anaesthetic agent. The chamber pressurizes above the critical pressure of carbon dioxide (72.9 bar) under the influence of a back-pressure regulator 608 situated downstream that keeps the circuit closed until a controllable pressure above the critical pressure is achieved.

Once the set pressure is achieved, the back pressure regulator 608 opens and supercritical $CO_2$ flows through the filter material 102 contained in the sleeve 501*a*, extracting the anaesthetic agent via the open valve 607*a*. Valve 607*b* is closed to prevent the passage of gas into the second chamber 502*b* and sleeve 501*b*. The supercritical solution 203 is then available for purification by supercritical fluid chromatography and/or fractional separation as described in P34906WO and this application.

The eluted anaesthetic agent concentration drops in an exponential decay and is measured by infrared spectroscopy 609 from feed 611*a*. When a set threshold is reached as determined by the controller 610 via feed 612*a* from IR detection 609, a signal 613*a* is sent to valve 607*a* and 606*a* (not shown) to close these valves. The controller then sends a signal (not shown) to the pump 614 that initiates the transfer of $CO_2$ and remaining anaesthetic agent from the first chamber 502*a* and sleeve 501*a* to the next chamber 502*b* and sleeve 501*b*. This transfer will initially be down a pressure gradient and will be passive, but will require energy after the gradient has equilibrated. When the pressure in the sleeve 501*a* and chamber 502*a* has reached atmospheric pressure, the pump 614 is stopped and flow discontinued.

The controller then signals (not shown) to valves 606*b* and 607*b* to open. Pressure in the circuit will have been maintained above critical pressure as the back pressure regulator 608 will have remained closed after flow through the first chamber 502*a* had ceased and the pressure dropped below the set-point for the valve to open. Once valves 606*b* and 607*b* are open, supercritical $CO_2$ will flow through the second chamber 502*b* and sleeve 501*b*, dissolving and extracting anaesthetic agent from the filter material 102. The supercritical solution 203 from chamber 502*b* is then available for purification by supercritical fluid chromatography and/or fractional separation as described in P34906WO and this application.

The system 600 has the benefit of not wasting remaining anaesthetic agent after elution/extraction has reached a set point. Therefore, the anaesthetic agent concentration set-point at which elution finishes can be set higher and high concentrations of anaesthetic agent can be maintained in the supercritical solution for subsequent chromatography steps. As chromatography purification is the rate-limiting step, this has a significant impact on efficiency. The system 600 also saves some of the energy and $CO_2$ required to pressurize the chambers, significantly reducing costs and environmental impact.

Figure 8:
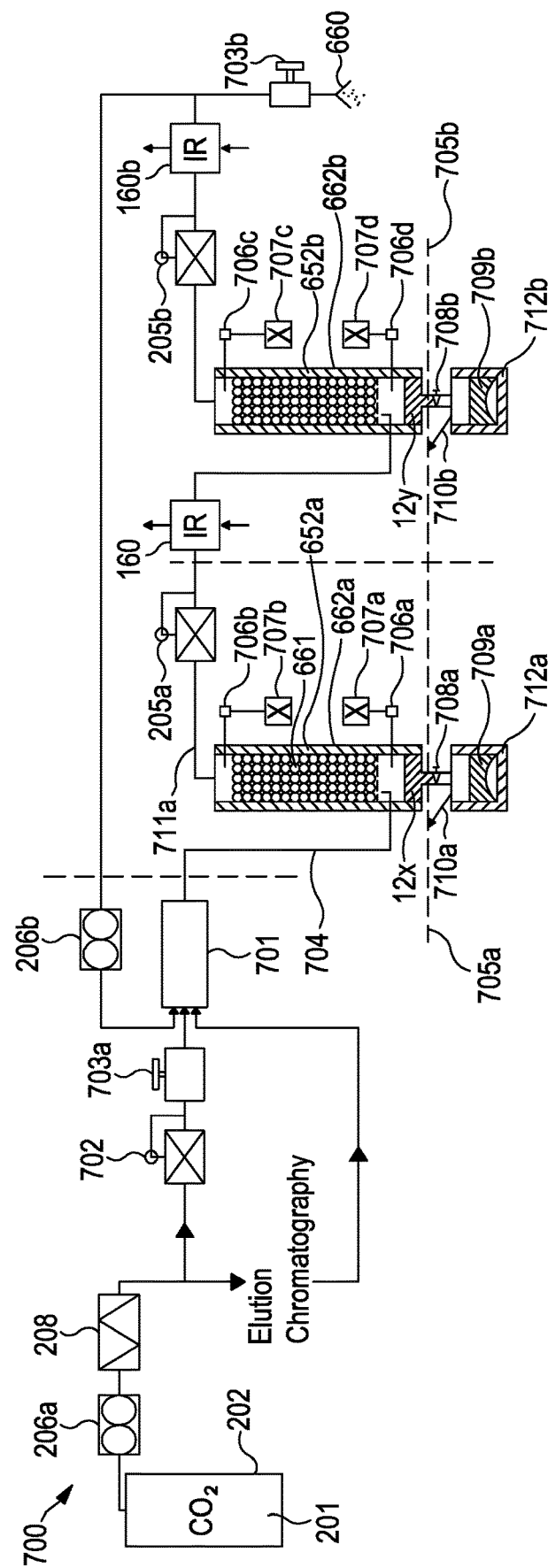
FIG. 8 is a schematic diagram of a supercritical fractionation system using an in-series system with the addition of an expansion vessel for the separation and condensation of anaesthetic agents.

The system 700 shown in FIG. 8 shows an in-series fractional separation and condensation system, including an expansion chamber and $CO_2$ recirculation, driven by the depressurization of supercritical $CO_2$, referred to as supercritical fractionation in P34906WO.

Carbon dioxide 201 from a pressurised cylinder 202 is fed to a pump 206*a*, increasing pressure to a set point above the critical pressure of $CO_2$ (72.9 bar). This fluid passes to an accumulator 208 in a temperature-controlled environment (not shown) above the critical temperature of $CO_2$ (31.1 degrees C.). The supercritical $CO_2$ from the accumulator passes into the elution and chromatography systems as described in P34906WO and this application. The supercritical $CO_2$ is used to elute/extract anaesthetic agent from a capture filter material and then purify it by multiple column supercritical fluid chromatography. Infra-red spectroscopy selects peaks corresponding to pure anaesthetic agent and these are delivered via a back pressure regulator to an expansion vessel 701. Another direct feed of $CO_2$ from the accumulator 208 is delivered to the expansion vessel 701 passing through a variable pressure-reduction valve 702 and safety valve 703*a* that protects the downstream circuit from supercritical pressures. Aliquots of a mixture of anaesthetic agents and gaseous $CO_2$ are delivered to the expansion vessel 701 when peaks are selected by IR spectrophotometer. The volume of the expansion vessel 701 and the direct flow of $CO_2$ from the accumulator 208 buffer this intermittent flow to produce a continuous flow of a mixture of anaesthetic agents carried in gaseous $CO_2$ from the expansion vessel 701 via an egress pipe 704. This mixture passes to the first fractionating column 652*a* containing inert beads 661 to turbulate flow and improve heat transfer for inertial condensation. The mixture is held at a pressure determined by a downstream pressure-reducing valve 205*a*. The pressure slows the flow of gases through the column to improve heat transfer and condensation of the anaesthetic gases. As this column is intended to selectively condense the least volatile anaesthetic agent, it is heated to prevent the more volatile fraction from condensing. This is by thermal sleeve 662*a* and a temperature-controlled environment 705*a*. The column temperature is measured by thermocouples 706*a*, 706*b* with readouts 707*a* and 707*b* respectively. The least volatile fraction 12*x* condenses and is collected by the opening of a needle valve 708*a* under computer control (not shown). The liquid anaesthetic agent passes into an expansion chamber 709*a* which increases its volume to maintain atmospheric pressure. The chamber 709*a* is maintained in a cold sleeve 712*a* to keep the purified anaesthetic agent 12*x* in liquid form while dissolved $CO_2$ is released for venting 710a. It is then checked for purity using gas chromatography-mass spectrometry (GC-MS) and bottled (not shown). Alternatively the liquid can be collected into a temperature controlled collection and depressurisation system as shown in FIGS. 3 and 4.

The more volatile anaesthetic agent and gaseous $CO_2$ leave the column 652a via an egress pipe 711a to the pressure-reducing valve 205a and an IR sensor 160 to ensure the absence of the least volatile fraction. The mixture passes into the second fractionation column 652b held at a lower pressure than the first fractionation column by a pressure reduction valve 205b. The second fractionation column is cooled by a temperature-controlled environment 705b and thermal sleeve 662b. Column intake and exit temperatures are measured by thermocouples 706c and 706d with respective readouts 707c and 707d. The condensed fraction 12y is collected at the bottom of the column and is transferred to an expansion chamber 709b by needle valve 708b under computer control (not shown). This chamber is cooled using a thermal sleeve 712b to keep the anaesthetic agent liquid while the gaseous $CO_2$ is vented 710b. Alternatively the liquid can be collected into a temperature controlled collection and depressurisation system as shown in FIGS. 3 and 4.

The pure $CO_2$ leaves the fractionation column 652b via the pressure-reducing valve 205b and IR chamber 160b to pass either back to the expansion chamber via a pump 206b to reduce the need for $CO_2$ via the direct feed from the accumulator 208. Thereby the direct feed is replaced by the recirculated feed. If the pressure in the circuit rises above a set threshold, pure $CO_2$ is vented to the environment 122 via a pressure safety valve 703b and vent 660.

Further purification can be achieved by fractional distillation (not shown).

Figure 9:
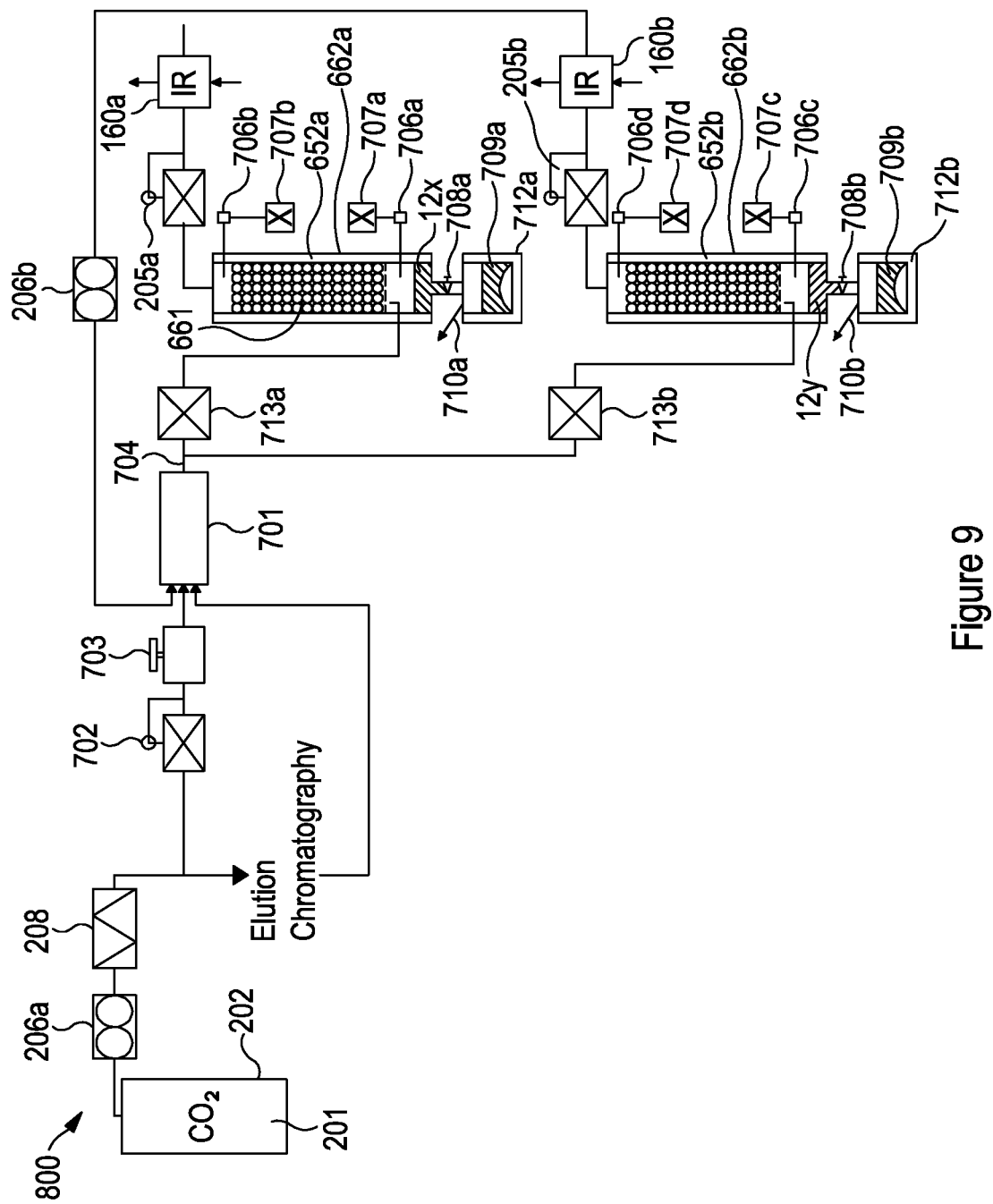
FIG. 9 is a schematic diagram of a supercritical fractionation system using a parallel recirculation system for the separation and condensation of anaesthetic agents.

The system 800 shown in FIG. 9 details a parallel anaesthetic agent fraction collection system using the sequential depressurization of $CO_2$, so called supercritical fractionation in patent P34906WO.

Carbon dioxide 201 stored in a pressurised cylinder 202 is fed to a pump 206a to raise the pressure to a set point above the critical pressure of $CO_2$ (72.9 bar). This is then fed to an accumulator 208 in a temperature-controlled environment (not shown) above the critical temperature of $CO_2$ (31.1 degrees C.). The supercritical $CO_2$ from the accumulator passes into the elution and chromatography systems as described in P34906WO and this application. The supercritical $CO_2$ is used to elute anaesthetic agent from a capture filter material and then purify it by multiple column supercritical fluid chromatography. Infra-red spectroscopy selects peaks corresponding to pure anaesthetic agent and these are delivered via a back pressure regulator to an expansion vessel 701. Another direct feed of $CO_2$ from the accumulator 208 is delivered to the expansion vessel 701 passing through a variable pressure-reduction valve 702 and safety valve 703 that protects the downstream circuit from supercritical pressures. Aliquots of a mixture of anaesthetic agents and gaseous $CO_2$ are delivered to the expansion vessel 701 when peaks are selected by IR spectrophotometer. The volume of the expansion vessel 701 and the direct flow of $CO_2$ from the accumulator 208 buffer this intermittent flow to produce a continuous flow of a mixture of anaesthetic agents carried in gaseous $CO_2$ from the expansion vessel 701 via an egress pipe 704 to a computer controlled valve 713a. This directs the mixture into the first fractionation column 652a containing inert beads 661 under a pressure set by the back pressure regulator 205a. The column is heated to prevent the condensation of the more volatile fraction of anaesthetic gas. This is achieved by the column being in a temperature-controlled environment (not shown) and being surrounded by a thermal sleeve 662a. Column temperature is measured by thermocouples 706a and 706b and read-outs 707a and 707b. The less volatile fraction 12x condenses and is collected at the bottom of the fractionation column 652a. It is released into an expansion chamber 709a via a needle valve 708a under computer control (not shown). The expansion of the chamber volume ensures that pressure remains at atmospheric pressure. The anaesthetic agent is cooled by a thermal sleeve 712a to prevent the anaesthetic agent vapourising as the $CO_2$ dissolved in the anaesthetic agent is vaporised. This $CO_2$ is vented 710a.

The column is set up to ensure that none of the more volatile fraction is collected at the expense of the possibility that not all the less volatile fraction is collected. Therefore, gas exiting the first fractionating column 652a is checked by IR 160 and if some of the less volatile fraction remains, it is passed back to a pump 206b and delivered to the expansion chamber 701 to go back through the valve 713a and into the first fractionation column 652a again. By multiple passes through the first fractionation column, complete condensation of the less volatile anaesthetic agent should be achieved without contamination by the more volatile fraction.

When all the less volatile fraction has been condensed, a controller (not shown) closes valve 713a and opens valve 713b, passing the $CO_2$ and the more volatile fraction into the second fractionating column 652b. This is at a pressure controlled by the back pressure regulator 205b. The temperature of the column is −30 to −20 degrees Celsius, controlled by a temperature-controlled environment (not shown) and thermal sleeve 662b and measured by thermocouples 706c, 706d and read-outs 707c and 707d respectively. The more volatile fraction condenses 12y, leaving gaseous pure $CO_2$ to pass out of the column. The fraction 12y collects at the bottom of the column and passes into an expansion chamber 709b via a needle valve 708b under computer control (not shown). The expansion of the chamber volume ensures that pressure remains at atmospheric pressure. The anaesthetic agent is cooled by a thermal sleeve 712b to prevent the anaesthetic agent vapourising as the $CO_2$ dissolved in the anaesthetic agent is vaporised. This $CO_2$ is vented 710b. It may be that some anaesthetic agent remains with the gaseous $CO_2$. This is detected by the IR detector 160b after passing through the pressure-reducing valve 205b. This signals to a controller (not shown) that recirculates the gases back to a pump 206b and the expansion chamber 701 to pass through the column 652b again and complete condensation over one or more cycles.

One advantage of system 800 over system 700 is that a pressure-reduction is not required between the first and second fractionation columns. By using a parallel system, the pressure and temperatures can be independently altered to condense the different agents at easily attainable temperatures and flow rates.

A further advantage of the preferred embodiment is that system 800 allows for incomplete condensation which is a likely occurrence. By using recirculation, system 800 can carefully and completely condense individual fractions of anaesthetic agent.

Figure 10:
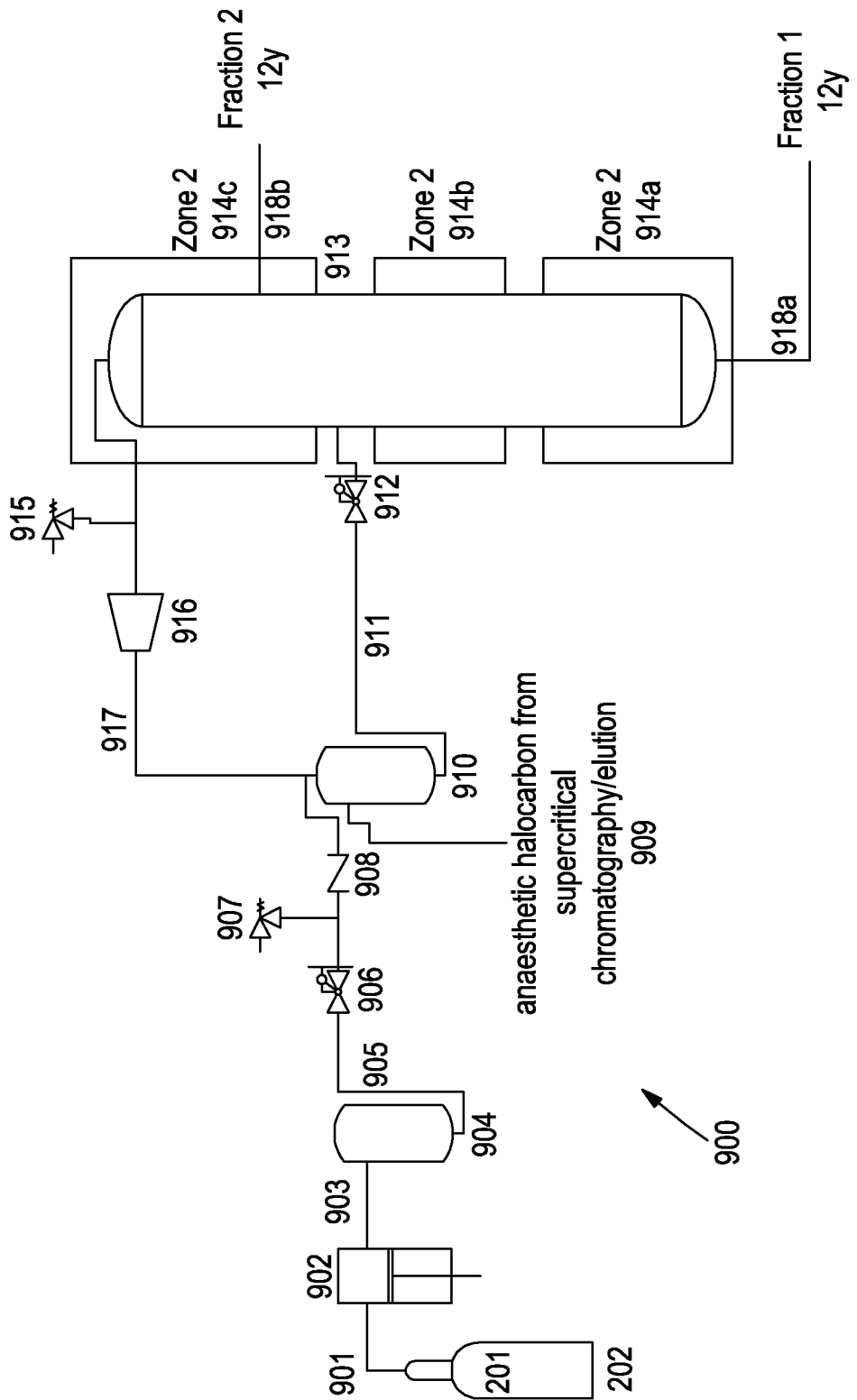
FIG. 10 is a schematic diagram of a single stage fractionation column for separating two fractions (Sevoflurane/Isoflurane from Desflurane) by using their respective boiling points, driven by the flow of $CO_2$.

FIG. 10 shows a single column schematic for the separation of different anaesthetic halocarbons by virtue of their different volatilities as shown in system 900.

Carbon dioxide 201 from a cylinder 202 and pipe 901 is pumped 902 via pipe 903 into an accumulator 904 at supercritical pressures. This may feed chromatography or elution steps as described in this patent as well as this current use (not shown). $CO_2$ passes through a transfer line 905 to a pressure reducing valve 906 reducing the pressure to 40-50 bar and one way valve 908 into another accumulator 910 under pressure relief valve 907 to prevent system overpressure.

The accumulator is fed with anaesthetic from the chromatography or elution systems 909 as described above. The accumulator buffers the pressures in the system and feeds the mixture of $CO_2$ and anaesthetic halocarbon through a transfer line 911 to a pressure reducing valve 912 dropping the pressure to 2-10 bar immediately adjacent to or incorporated into the fractionation column 913 under the protection of a pressure relief valve 915. The pressure drop and adiabatic expansion cause the temperature of the gas to drop to −20 to −30 degrees Celsius. Both anaesthetic fractions 12*x* and 12*y* condense in the column and pass by gravity down the column 913. The column is temperature controlled by thermal sleeve (not shown) into three separate zones 914*a, b, c*. The temperature of zone 1, 914*a*, is near the boiling point of the less volatile fraction, in this case Desflurane at 23 degrees Celsius. Thus, Sevoflurane or Isoflurane (fraction 12*x*) will collect and be available for removal and final removal of $CO_2$ as described elsewhere in this application by the pipe 918*a*. The Desflurane boils and passes back up the column through zone 2, held at an intermediate temperature between the boiling point of Desflurane and the temperature at which the saturated vapour pressure of Desflurane is zero (around −30 degrees Celsius). The Sevoflurane/Isoflurane condenses and passes back down the column. The Desflurane proceeds up to zone 3, at a temperature of −20 to −30 degrees Celsius, where the Desflurane condenses and is removed by transfer line 918*b* to form fraction 12*y*. Gaseous $CO_2$ leaves the column and passes to a compressor 916 where it is re-pressurised to 40-50 bar and passes back via pipe 917 to the accumulator 910 to form a continuous loop, to reduce the need for input from the cylinder $CO_2$. This may be under microprocessor control (not shown).

Figure 11A:
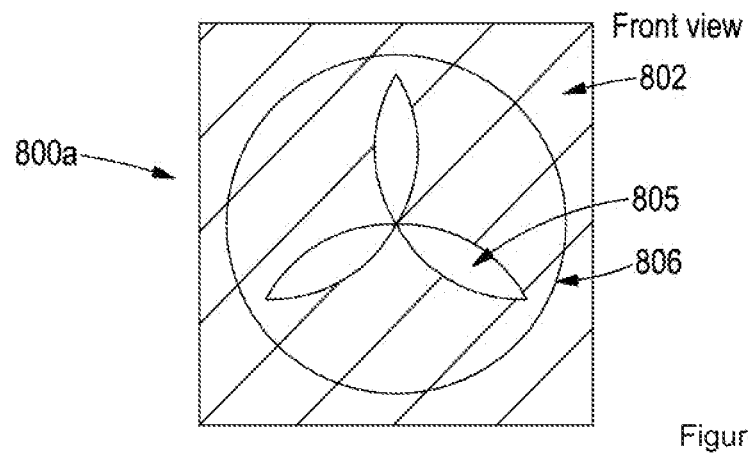
FIGS. 11A-11C show a schematic diagram of a housing to collect halocarbons and nitrous oxide intermediates onto a capture material by using the air drawn by a fan in a vehicle or air conditioning unit.
Figure 11B:
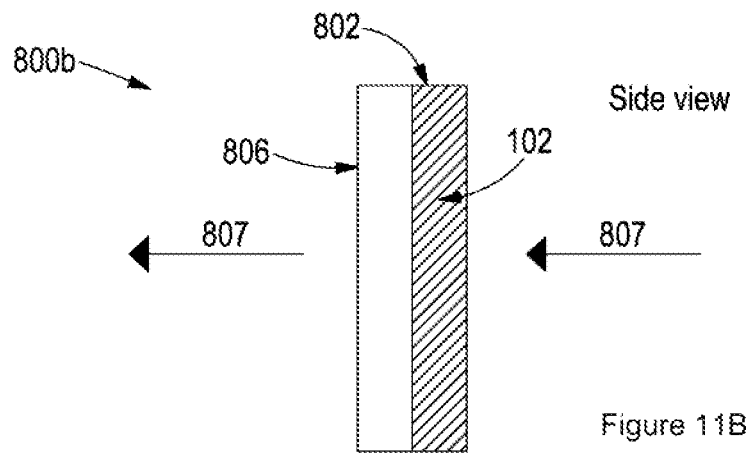
Figure 11C:
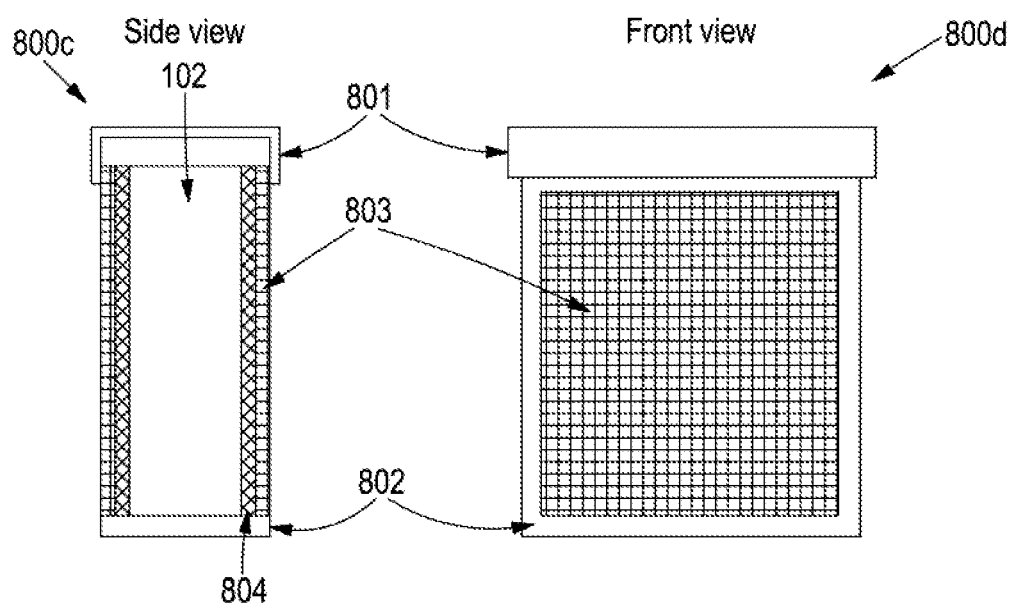

FIGS. 11A-11C show a system 800*a* and 800*b* demonstrating a front (800*a*) and side view (800*b*) of a fan 805 in assembly 806 behind an enclosure 802 filled with filter material 102. The enclosure is fitted so that air flow 807 passes through the enclosure. This could be arranged so that air passes from the fan to the enclosure or from the enclosure to the fan (as shown in 800*b*) depending on available configurations.

Diagram 800*c* and *d* show the side 800*c* and front view 800*d* of the enclosure 802, with the front and back of the enclosure being made of a wide-grid mesh 803 supporting a fine mesh 804 capable of containing the capture material 102. The enclosure shape and size would depend on what fan unit it was to be attached to and would be made to ensure that the resistance to airflow of the mesh and capture material did not reduce airflow to the machine excessively.

Figure 12:
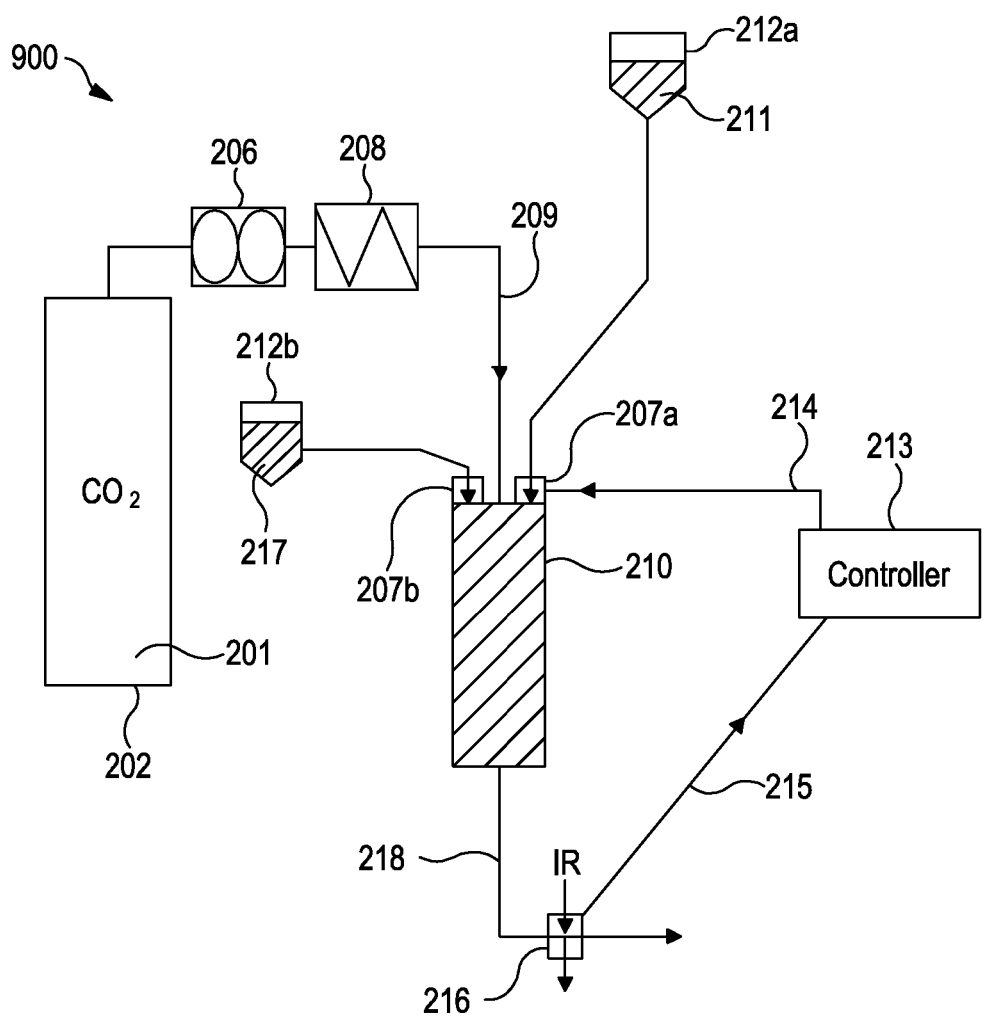
FIG. 12 is a schematic diagram of a system for manufacturing and purifying sevoflurane from chlorosevoether (chloromethyl 2,2,2-trifluoro-1-(trifluoromethyl)ethyl ether dissolved in supercritical $CO_2$ reacted with a sterically-hindered tertiary amine hydrofluoride.

System 900 for the manufacture of sevoflurane from chlorosevoether is shown in FIG. 12. Carbon dioxide 201 contained in a cylinder 202 passes through a pump 206 to increase the pressure above the critical pressure of $CO_2$ (72.9 bar). The fluid enters an accumulator 208 in a temperature-controlled environment (not shown) above the critical temperature of $CO_2$ (31.1 degrees Centigrade). The supercritical $CO_2$ leaves the accumulator 208 via egress conduit 209 into the reaction chamber 210 made of a pressure and temperature tolerant material, preferably although not exclusively stainless steel or aluminium, and coated in an inert material, preferably but not limited to Teflon, polyimide, polyethylene napthalate or another material that does not react with fluoroethers or supercritical carbon dioxide. Chlorosevoether 211 contained in an inert vessel 212*a* is injected into the reaction vessel 210 by a high pressure pump (not shown) and injector 207*a* under the signal 214 of a controller 213. This controller is influenced by the output 215 of a detector 216, preferably UV, MS, PAS or ARS but most favourably IR spectroscopy. Further reagent, in the form of a tertiary amine hydrofluoride salt 217 contained in an inert container 212*b* is injected into the reaction vessel 210 by a high-pressure pump (not shown) and injector 207*b* under the influence of the controller 213 (not shown). The reaction proceeds inside the reaction vessel at temperatures above the critical temperature of carbon dioxide (31.1 degrees Centigrade) and at pressures above the critical pressure of carbon dioxide (72.9 bar). Products and reactants proceed through the chamber under the flow of supercritical $CO_2$ and reactants. This delivers the supercritical solution 218 to the detector 216 to regulate the input of reagent and reaction conditions. The reaction temperature can be altered by changing the temperature of the environment, although it must remain above the critical temperature of $CO_2$. The pressure of the reaction can be altered by the controller influencing the pump 206. The supercritical solution 218 is delivered to chromatography and/or fractional separation modules as shown in FIG. 4, 8, 9 or 10.

Figure 13:
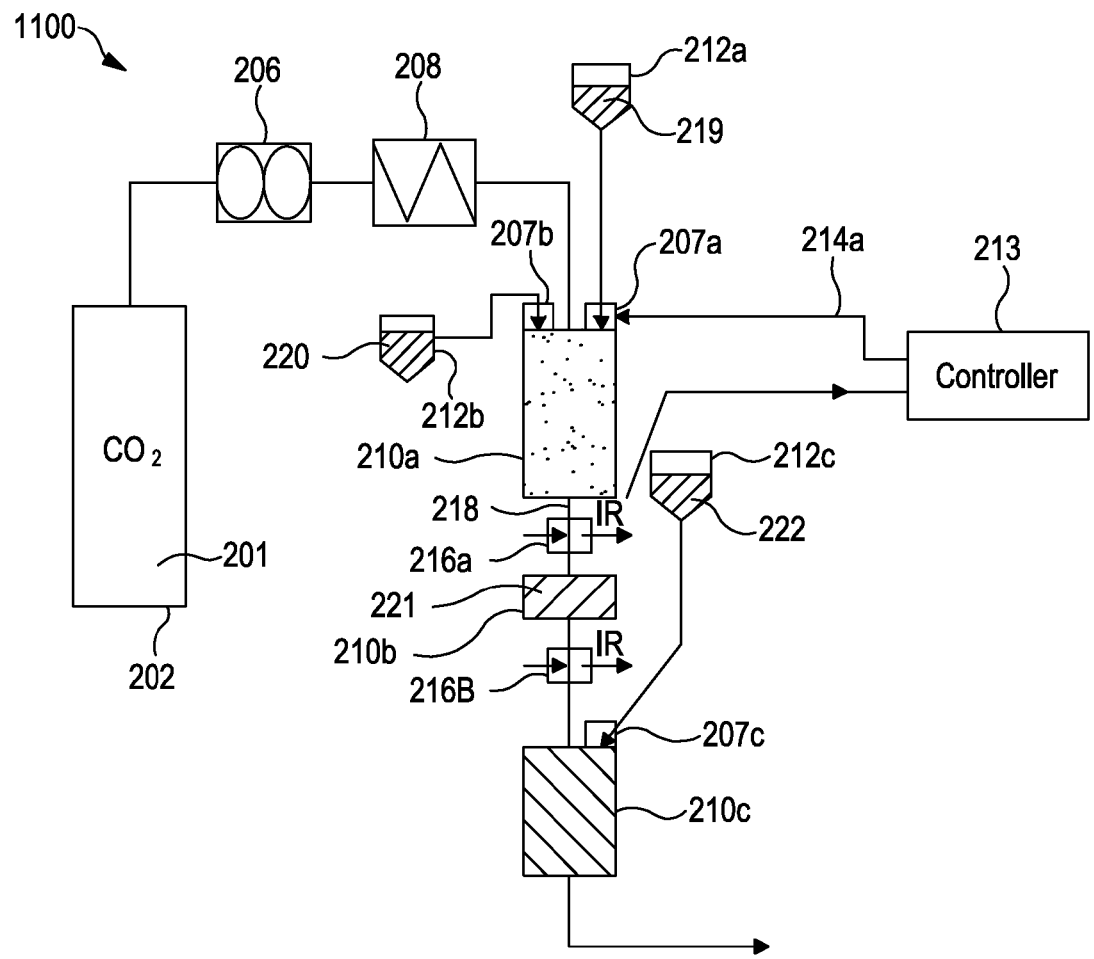
FIG. 13 is a schematic diagram of a system for the manufacture and purification of sevoflurane from hexaflouroisopropanol (HFIP) with equimolar or excess molar concentrations of paraldehyde or trioxane in the presence of aluminium trichloride to form sevochlorane with subsequent fluoro-substitution by potassium fluoride.

The system 1000 shows the process of manufacture of sevoflurane from hexafluoroisopropanol (HFIP) in FIG. 13. Carbon dioxide 201 contained in a pressurised cylinder 202 is transferred above critical pressure (72.9 bar) by a pump 206 and passed into an accumulator 208 in a temperature controlled environment (not shown) above the critical temperature of carbon dioxide (31.1 degrees Centigrade). Supercritical $CO_2$ passes into a first reaction chamber 210*a* made of a pressure and temperature tolerant material, preferably although not exclusively stainless steel or aluminium, and coated in an inert material, preferably but not limited to Teflon or another material that does not react with fluoroethers or supercritical carbon dioxide. HFIP 219 in an inert container 212*a* is fed into the reaction chamber by a high-pressure pump (not shown) and injector 207*a* under the signal 214*a* from a controller 213. Formaldehyde, preferably paraformaldehyde or trioxane 220 contained in an inert container 212*b*, in equimolar or molar excess quantities are also fed into the first reaction chamber 210*a* by high-pressure pump (not shown) and injector 207*b* under the control of the controller 213 (signal not shown). The supercritical solution 218 passes from the reaction chamber via a detection device 216*a* preferably UV, MS, PAS or ARS but most favourably IR spectroscopy into a second reaction chamber 210*b* containing aluminium trichloride to produce sevochlorane dissolved in supercritical $CO_2$. The products pass through a second detector 216*b* into a third reaction chamber 210*c* in which potassium fluoride 222 contained in an inert container 212*c* and dissolved in water is fed into the chamber by high-pressure pump and injector 207*c*. Water will quench the reaction of any remaining aluminium hyroxydichloride with sevochlorane. Alternatively solid potassium fluoride could be present inside the third reaction vessel 210*c*. Sevochlorane reacts with the fluorine-donor to produce sevoflurane. Products leave the third reaction chamber to further supercritical chromatography or fractionation for example as shown in FIG. 4, 8, 9 or 10.

Figure 14:
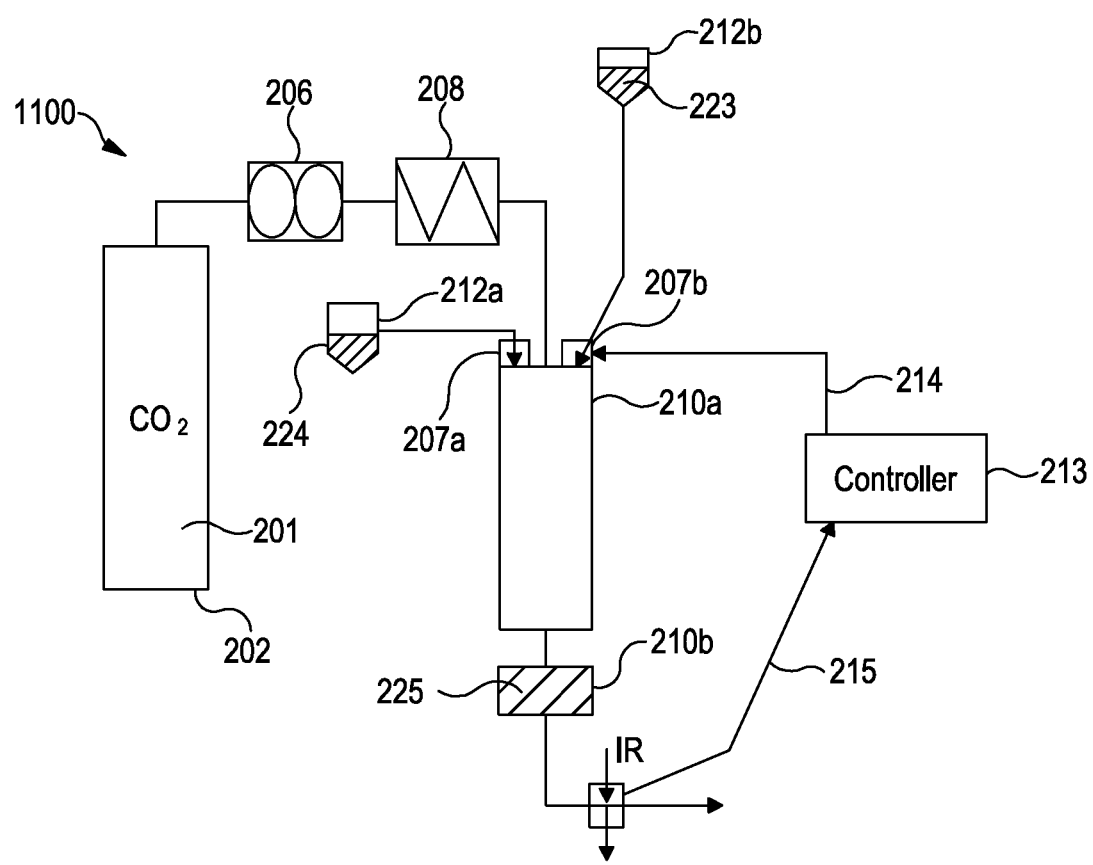
FIG. 14 is a schematic diagram of a system for the manufacture and purification of desflurane from isoflurane and anhydrous hydrogen fluoride or alkali metal fluoride using a suitable catalyst.

The system 1100 shown in FIG. 14 shows a method for the manufacture of desflurane from isoflurane and a fluorine donor, preferably potassium fluoride, sodium fluoride or anhydrous fluorine. Carbon dioxide 201 contained in a pressurised cylinder 202 is transferred above critical pressure (72.9 bar) by a pump 206 and passed into an accumulator 208 in a temperature controlled environment (not shown) above the critical temperature of carbon dioxide (31.1 degrees Centigrade). Supercritical $CO_2$ passes into a first reaction chamber 210a made of a pressure and temperature tolerant material, preferably although not exclusively stainless steel or aluminium, and coated in an inert material, preferably but not limited to Teflon or another material that does not react with fluoroethers or supercritical carbon dioxide.

Isoflurane 224 contained in an inert container 212a is injected into the reaction vessel by high-pressure pump (not shown) and injector 207a, dissolving into the supercritical $CO_2$. A fluorine donor 223, preferably hydrogen fluoride, potassium fluoride, sodium fluoride or anhydrous fluorine, contained in an inert container 212b is injected into the reaction chamber 210a by a high-pressure pump and injector 207b. Alternatively the potassium fluoride may be present as a granular solid in the reaction vessel 210a. The fluorotransfer reaction may proceed without catalysis, but may require transfer of the reactants into a second reaction chamber 210b, containing a catalyst 225, preferably but not limited to antimony pentahalide, a transition metal trifluoride (for example cobalt trifluoride), transition metal oxide (such as chromia) or mixed with a phase transfer catalyst such as tetramethylammonium chloride. In a preferable embodiment, these catalysts are present inside the reaction chamber 210a with the potassium fluoride, removing the need for a second reaction chamber 210b. Products including desflurane pass through a detection device 216 preferably UV, MS, PAS or ARS but most favourably IR spectroscopy that relays 215 to a controller 213 to signal 214 and regulate the pump 206 pressures (not shown), the temperature (not shown) and the injectors 207a (not shown) and 207b to control the flow of reactants and solvent into the reaction vessel 210a. The products then pass into the supercritical chromatography and/or fractionation systems for example as shown in FIGS. 4, 8, 9 and 10.

Figure 15A:
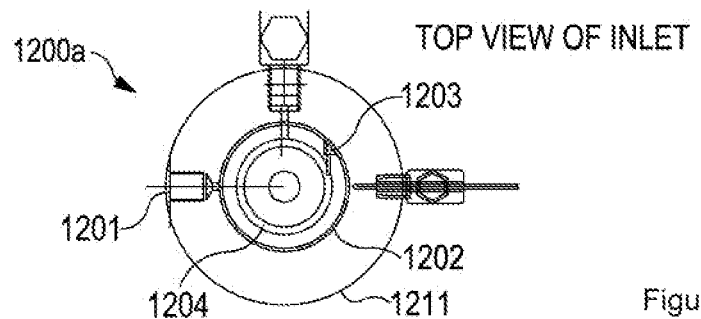
FIGS. 15A-15B show a cooled gas liquid separator for the separation of liquid anaesthetic halocarbon from gaseous carbon dioxide.
Figure 15B:
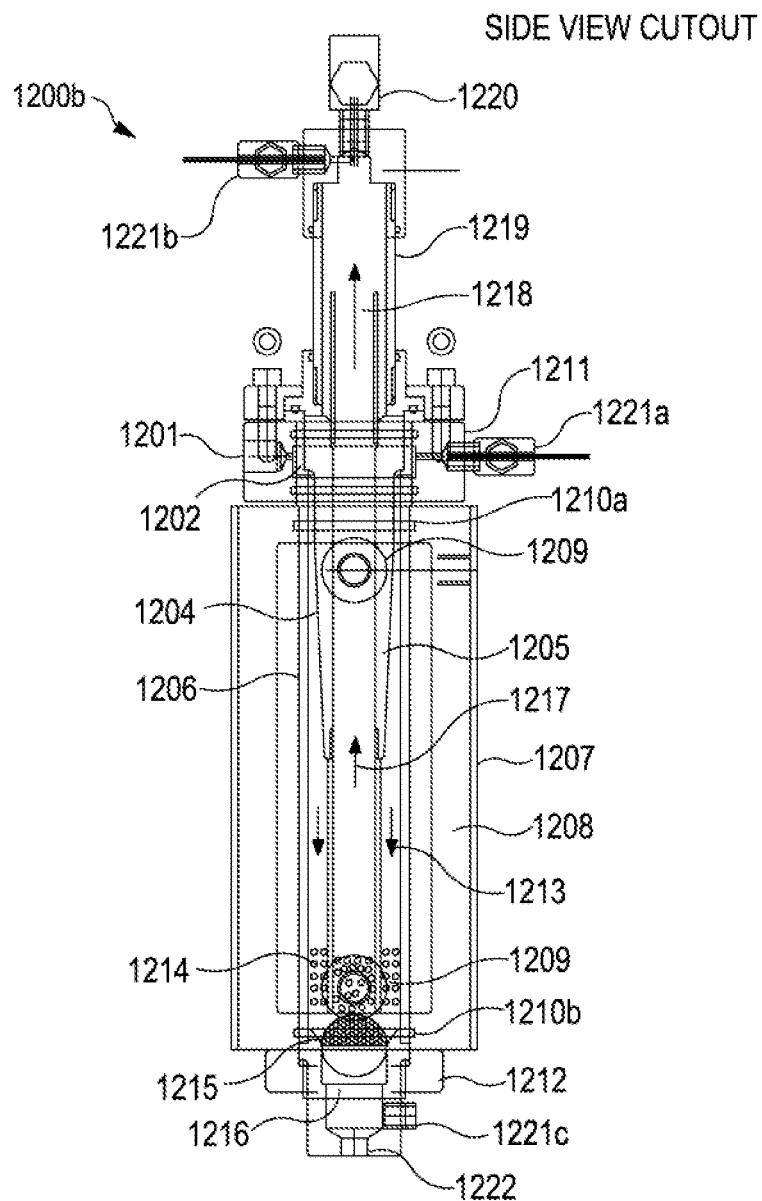

A device for the separation of liquid anaesthetic halocarbons from gaseous CO2 is shown in FIGS. 15A-5B, with a top view of the inlet 1200a and a side-view cutout of the entire device 1200b.

The mixture of CO2 and anaesthetic agents (plus contaminants depending on the stage of the process that the device is being used in) is depressurised immediately adjacent to the gas liquid separator (GLS) 1200a, b. The gas mixture enters the GLS via a input connector 1201, the gas entering a circular chamber 1202 with three eccentric injector ports 1203 that pass from the circular chamber 1202 into the cyclonic chamber 1204. The cyclonic chamber is a tube with a tapered central pipe 1205 that ensures that the upper portion of the chamber sectional area is small, so that when combined with the eccentric injection of the gas mixture, it forms a cyclonic motion. As the mixture is decompressed through the pressure reducing valve before the GLS (not shown) and the narrow eccentric inlet ports 1203, it undergoes adiabatic expansion and cools to −20 to −30 degrees Celsius. The anaesthetic halocarbon condenses and is passed onto the outer surface 1206 of the cyclonic chamber 1204 by the cyclonic rotation of the CO2 gas. This outer surface 1206 is cooled to −20 to −30 degrees Celsius by a thermal jacket 1207 that contains a coolant such as Polyethylene Glycol 1208 cooled by connection 1209 to an external chiller unit (not shown). The jacket is sealed top 1210a and bottom 1210b and held in place against the injector assembly 1211 by a screw on lower element 1212.

The CO2 gas passes down the cyclonic chamber (arrow 1213), the sectional diameter increases and the gas velocity slows until it reaches cooled glass beads 1214 that provide inertial condensation and also protect condensed anaesthetic halocarbon that has passed down the outer surface 1206 from exposure to further rapid gas flow. The beads are held in place by a mesh 1215 that covers the outlet 1216. CO2 gas then passes up the tapered central pipe 1205 (arrow 1217), past the coldest area of the GLS near the injection and expansion point of the gas mixture 1211, leading to further condensation. The gas velocity in the central tapered pipe is such that a bead of liquid will be able to run down the inner surface of the pipe 1205. CO2 gas exits the central pipe (arrow 1218) in the uppermost section 1219 and leaves the assembly by a connector 1220 for subsequent recompression and re-use. The entire assembly is pressure tolerant with working pressure of up to 20 bar for areas exposed to the CO2. This pressure is maintained by a pressure-relief valve (not shown) located following the gas outlet 1220. Temperature in the GLS is monitored by thermocouples 1221a, b, c. The liquid outlet 1216 passes to a output pipe 1222 (only the start is shown), that is subsequently connected to a valve (not shown). The GLS can be completely disassembled for cleaning and quality control checks as required. The main body of the GLS is made from 316 stainless steel, the injector section 1211 is made from anodised aluminium and the thermal jacket is made from PTFE (Polytetrafluoroethylene) with a stainless steel cover, however other suitable materials could be used known to those skilled in the art.

Experimental Information

A 316 stainless steel 1 Litre internal volume capture sleeve containing plain silica gel granules (0.5-1 mm) was connected to the anaesthetic exhaust, before a charcoal canister in a veterinary medical environment. The capture vessel was in place for 7 working days and gained 118 g of weight. Expected anaesthetic consumption during this period was 80-130 g during normal use. Anaesthesia consisted of 2 L/min oxygen with 2% sevoflurane via veterinary circle system and soda lime $CO_2$ absorber.

The contents of the sleeve were extracted using supercritical $CO_2$ at 80 bar and 50° C. for 90 minutes with >90% of product produced during the first 40 minutes.

Gas liquid separator jacket temperature was controlled at −20° C. Input pressure to pressure reducing valve before gas-liquid separator was 40-50 bar set by digital pressure switch regulating solenoid input from $CO_2$ cylinder (44-50 bar). Pressure reduced to 10 bar in gas liquid separator. Gas input temperature −21 to −32° C. with gas output temperatures of −14 to −20° C.

Carbon dioxide was recirculated by a Haskel AG-30 single stage, lubrication free gas booster with air drive pressure of 6 bar.

100-105 mL of product was recovered. Gas Chromatography-FID showed purity of 99.7%, Gas Chromatography-Mass Spectrometry showed major contaminant as HFIP (Hexafluoroisopropanol).

Example chromatography separation results for demonstration using JASCO PU-2080 SFC equipment with UV or IR detection:

Separation of common exhaled contaminants:
Cyano column 100 mm length, 21 mm ID—flow 20 mL/min, 80 bar, 55° C., 2 mL injection volume
Sevoflurane and Isoflurane—0.4-1.5 min
Ethanol 0.1%-6-9 mins
Methanol 0.1%-7.5-9 mins
Acetone 0.05%-3-4 mins Separation of HFIP from anaesthetic agents:

Cyano column 250 mm length 4.6 mmID—flow 0.5 mL/min, 80 bar, 40° C., 10 microlitre separate injection volume Isoflurane/Sevoflurane 7.5 min-1.5 min HFIP 16-35 mins Separation of Sevoflurane from Isoflurane:

DEAP 2×250 mm 4.6 mmID flow rate 2.9 ml/min $CO_2$, 0.1 ml/min ethanol, 80 bar, 40° C., injection 50:50 isoflurane:sevoflurane, 10 microlitres volume.

Sevoflurane 2.2-2.5 mins

Isoflurane 2.7-3.1 min

Although illustrative embodiments of the invention have been disclosed in detail herein, with reference to the accompanying drawings, it is understood that the invention is not limited to the precise embodiment shown and that various changes and modifications can be affected therein by one skilled in the art without departing from the scope of the invention as defined by the appended claims and their equivalents.

The invention claimed is:

1. An anaesthetic halocarbon capture system for the remanufacture of anaesthetic agents, comprising:
    a pressure-intolerant sleeve containing filter material for capturing one or more types of anaesthetic halocarbon; and
    a pressure-tolerant housing that is tolerant of supercritical pressures above 73 bar; and
    into which the pressure-intolerant sleeve is inserted so as to permit exposure of the pressure-intolerant sleeve contents to pressures required for extraction of the anaesthetic halocarbon by supercritical fluid carbon dioxide;
    wherein the pressure-intolerant sleeve is locatable remotely from the pressure-tolerant housing;
    wherein the pressure intolerant sleeve comprises two ends and a cap at each of the ends;
    wherein the pressure-tolerant housing comprises a base and a moulded lid, the base comprising a moulded insert shaped to accept one of the caps, the moulded lid shaped to accept the other cap, and the moulded insert and the lid each comprising channels;
    wherein each cap is mobile on a seal that is capable of moving when pressurised to engage and seal the pressure-intolerant sleeve into the moulding in the pressure-tolerant housing to ensure that flow of the supercritical fluid only proceeds internally through the sleeve.

2. The anaesthetic halocarbon capture system of claim 1, in which the system receives exhaust of an anaesthetic circuit.

3. The anaesthetic halocarbon capture system of claim 1, wherein the pressure-tolerant housing is a stainless steel tube.

4. The anaesthetic halocarbon capture system of claim 1, wherein the filter material is selected from: granular silica, zeolite, carbon, activated carbon, aerogel, a metal, or a metal oxide.

5. The anaesthetic halocarbon capture system of claim 1, wherein the pressure-intolerant sleeve is arranged to allow ingress and egress of gas containing anaesthetic halocarbon and supercritical fluid through the filter material, in which the pressure-intolerant sleeve comprises a first conduit and a second conduit, wherein the first conduit allows gas to ingress into the sleeve and supercritical fluid to egress the sleeve and the second conduit allows gas to egress the sleeve and supercritical fluid to ingress into the sleeve.

6. The anaesthetic halocarbon capture system of claim 1, wherein the pressure-intolerant sleeve comprises a first pair of conduits and a second pair of conduits, the first pair of conduits allows the ingress and egress of gas, and the second pair of conduits allows the ingress and egress of supercritical fluid.

7. The anaesthetic halocarbon capture system of claim 1, wherein the pressure-intolerant sleeve or the anaesthetic halocarbon introduced into the pressure-intolerant sleeve is cooled during collection.

8. The anaesthetic halocarbon capture system of claim 1, further comprising a device for separating the anaesthetic halocarbons from the supercritical fluid following extraction.

9. The system of claim 2, wherein the anaesthetic circuit is a Mapleson circuit or an anaesthetic reflector system.

10. The anaesthetic halocarbon capture system of claim 1, further comprising a gas-liquid separator, comprised of a cooled cyclonic and inertial collection system.

11. The anaesthetic halocarbon capture system of claim 1, further comprising one or more separating columns.

12. The anaesthetic halocarbon capture system of claim 1, wherein the pressure-intolerant sleeve further comprises a gas ingress port and a gas egress port.

13. An anaesthetic halocarbon capture system comprising:
    a pressure-intolerant sleeve containing filter material for capturing one or more types of anaesthetic halocarbon; and
    a pressure-tolerant tube that is tolerant of supercritical pressures above 73 bar and into which the pressure-intolerant sleeve is inserted so as to permit exposure of the pressure-intolerant tube contents to pressures required for extraction of the said one or more types of anaesthetic halocarbon from said filter material by supercritical fluid carbon dioxide;
    wherein the pressure-intolerant tube is located remotely from the pressure-tolerant tube during capture of said one or more types of anaesthetic halocarbon; and
    wherein the pressure-intolerant sleeve comprises two ends each having an end cap, wherein once the filter material is loaded with captured anaesthetic halocarbon the pressure-intolerant sleeve is loaded into the pressure-tolerant tube, and wherein the pressure-intolerant sleeve is configured to be sealed into the pressure-tolerant tube by one or both of the end caps.

* * * * *